United States Patent
Shoemaker et al.

(10) Patent No.: US 8,349,326 B2
(45) Date of Patent: *Jan. 8, 2013

(54) METHODS AND SYSTEMS FOR MULTI-ANTIBODY THERAPIES

(75) Inventors: Charles B. Shoemaker, North Grafton, MA (US); Jean Mukherjee, Worcester, MA (US)

(73) Assignee: Tufts University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/889,511

(22) Filed: Sep. 24, 2010

(65) Prior Publication Data

US 2011/0129474 A1   Jun. 2, 2011

Related U.S. Application Data

(63) Continuation-in-part of application No. 12/032,744, filed on Feb. 18, 2008.

(60) Provisional application No. 60/890,626, filed on Feb. 20, 2007.

(51) Int. Cl.
*A61K 39/395* (2006.01)
*A61K 39/40* (2006.01)
*A61K 39/08* (2006.01)
*C12P 21/08* (2006.01)
*C07K 16/12* (2006.01)
*C07K 14/33* (2006.01)
*C07K 16/00* (2006.01)

(52) U.S. Cl. ............... 424/133.1; 424/135.1; 424/164.1; 424/167.1; 424/236.1; 424/247.1; 530/350; 530/388.4; 530/389.1; 530/389.5; 536/23.4; 536/23.53

(58) Field of Classification Search .................. None
See application file for complete search history.

(56) References Cited

U.S. PATENT DOCUMENTS 5,196,193 A * 3/1993 Carroll .................. 424/172.1
2006/0018911 A1 * 1/2006 Ault-Riche et al. ....... 424/178.1

OTHER PUBLICATIONS

Riemer et al, Mol. Immunol. 42: 1121-1124, 2005.*
Yu et al, Investigative Ophthalmology & Visual Science 49(2): 522-527, Feb. 2008.*
Witte et al, Cancer and Metastasis Reviews 17: 155-161, 1998.*
Stancovski et al, Proceedings of the National Academy of Science USA 88: 8691-8695, 1991.*
M. Clark. "Animal Models" 1998 [retrieved online May 23, 2008]. Retrieved from the Internet URL: http://www.path.cam.ac.uk/~mrc7/iggfunctions/models.html.
A. Nowakowski et al. "Potent neutralization of botulinum neurotoxin by recombinant oligoclonal antibody", PNAS, 99(17):11346-11350 (Aug. 20, 2002).
Cohn, M., and Langman, R.E., "The immune system: A look from a distance", Frontiers in Bioscience 1, d318-323 (Oct. 1, 1996).
Tonegawa, S., "The genetic principle for generation of antibody diversity", The Nobel Assembly at the Karolinska Institute [online], 1987 [retrieved on May 23, 2008]. Retrieved from the Internet <URL:http://nobelprize.org/nobel_prizes/medicine/laureates/1987/press.html>.

* cited by examiner

*Primary Examiner* — Phuong Huynh
(74) *Attorney, Agent, or Firm* — Sonia K. Guterman; Teofilo Javier, Jr.; Lawson & Weitzen LLP

(57) ABSTRACT

The present invention relates to methods and systems for administering antibody therapeutic agents. The methods include administering one or more (e.g., two or three) binding agents, wherein each of the binding agents has one or more monomers that have a binding region that is specific to a portion of a disease agent and one or more copies of a tag. The binding agents can be specific to one or more portions of the same or different disease agents. The tag is the same for each of the binding agents. The methods include administering an anti-tag antibody, wherein the anti-tag antibody has an anti-tag region that is specific to the tag, and can have an immunoglobulin (e.g., IgA, IgD, IgE, IgG, and IgM). Disease agents include bacteria, bacterial proteins, viruses, viral proteins, cancer cells, and proteins or toxins produced therefrom or from other sources such as snakes, insects, plants, etc. In particular, the present invention includes methods and systems for binding agents having one or more monomers that are specific to neurotoxins that cause botulism.

15 Claims, 18 Drawing Sheets

Anti-BoNT/A sheep scFv coding sequences

>scFv#2
CAGGCTGTGCTGACTCAGCCGTCCTCCGTGTCCGGGTCCCCGGGCCNNAGG
TCTCCATCACCTGCTCTGGAAGCAGGAGTAACGTTGGCACATATGGTGTAGG
TTGGTTCCAACAGCTCCCAGGATCGGGCCTCAGAACCATCATCTATTATAATG
ACAAACGACCCTCAGGGGTCCCCGACCGATTCTCTGCCTCCAAATCGGGCAA
CACAGCCACCCTGATCATCAGCTCGCTCCAGGCTGAGGATGAGGCCGATTAT
TTCTGTGGAAGTGCCGACGGTAGTAGTTATGGTATTTTCGGCAGTGGGACCA
GACTGACCGTCCTGGGTCAGCCCGCGGCCGCTGGTGGAGGCGGTTCAGGCGG
AGGTGGCTCTGGCGGTGGCGGATCGGCGCGCCAGGTGGGGCTGCAGGAGTCG
GGACCCAGCCTGGTGAAGCCCTCACAGACCCTCTCCCTCACCTGCACGGTCTC
TGGATTCTCATTGTCCAACAGTGTTGTAGGCTGGGTCCGCCAGGCTCCAGGAA
AGGTGCCGGAGTGGCTTGGTAGTATAGACAGTGGTGGTTACACAGTCGCTGA
CCCGGCCCTGAAATCCCGACTCAGCATCACAAGGGACACTTCCAAGAGCCAA
GTCTCCCTGTCACTGAACAGCGTGACAACTGAGGACACGGCCGTGTACTACT
GTACAAGGGCTTATAGTATTACTTATTATGCGTATCCCCCCTATATCGACTAC
TGGGGCCCAGGACTCCTGGTCACCGTCTCCTCAACTAGTGGTGCGCCGGTGC
CGTATCCGGATCCGCTGGAACCGCGTGCCGCA (SEQ ID NO:1)

>scFv#3
CAGGCTGTGCTGACTCAGCCGTCCTCCGTGTCCAGGTCCCTGGGCCAGAGTGT
CTCCATCACCTGCTCTGGAAGCAGCAGCAACGTTGGATATGGTGATTATGTG
GGCTGGTTCCAACGGGTCCCAGGATCAGCCCCCAAACTCCTCATCTATGGTG
CAACCACTCGAGCCTCGGGGGTCCCCGACCGATTCTCCGGCTCCAGGTCTGG
CAACACAGCGACTCTGACCATCAGCTCGCTCCAGGCTGAGGACGAGGCCGAT
TATTACTGTTCATCTTACGACAGTAGTCACTATAGTATTTTCGGCAGTGGGAC
CAGCCTGACCGTCCTGGGTCAGCCCGCGGCCGCTGGTGGAGGCGGTTCAGGC
GGAGGTGGCTCTGGCGGTGGCGGATCGGCGCGCCAGGTGGAGCTGCAGGAG
TCGGGACCCAGCCTGGTGAAGCCCTCACAGACCCTCTCCCTCACCTGCACGG
TCTCTGGATTCTCATTAAGTAGCAATGCTGTAGGCTGGGTCCGCCAGGCTCCA
GGAAAGGCGCCGGAGTGGGTTGGTGGTATAGATATAGATGGAAGGCCGGTCT
ATAAACCAGGCCTTAAGTCCCGGCTCAGCATCACCAGGGACACCTCCAACGC
TCAAGTCTCCCTGTCACTGAGCAGCGTGACAACTGAGGACACGGCCGTGTAC
TTCTGTGCAAGTTATTATGGTGGTTATCTTTATAATTATGCCCCTGGGGCATAT
ATCGAGCACTTGAGCCCAGGACTCCTGATCACCGTCTCCTCAACTAGTGGTGC
GCCGGTGCCGTATCCGGATCCGCTGGAAACCGCGTGCCGCA (SEQ ID NO:3)

Fig. 1A

\>scFv#7
TCCTATGAACTGACCCAGCCGCCTTCAATGTCGGTGGCCTTGGGACAGACGG
CCAAGGTCACCTGCCAGGGAGACAACTTAGAAAACTTTTATGTTCAGTGGCA
CCAGCAGAAGCCGGGCCAGGCCCCTGTGACGGTCATTTTTCAGGATAATAAG
AGGCCCTCGGGGATCCCTGACCGGTTCTCTGGCTCCAACTCGGGGAACACGG
CCACCCTGACCATCAGCGGGGCCCGGACCGAGGACGAGGCCGACTATTACTG
TCAGTCAGGCCACAGCAGTATCGGTGGTGTTTCGGCAGCGGGACCAGCCTG
ACCGTCCTGGGTCAGCCCGCGGCCGCTGGTGGAGGCGGTTCAGGCGGAGGTG
GCTCTGGCGGTGGCGGATCGGCGCGCCAGGTGCAGCTGCAGGAGTCGGGACC
CAGCCTGGTGAAGCCCTCACAGACCCTCTCCCTCACCTGCACGGTCTCTGGCT
TCTCATTAACGGGAAATTCTGTAACCTGGGTCCGCCAGGCTCCAGGAAACGT
GCCGGAGTGGCTTGGTGGTATAAGCCGCGGTGGACGCACATACTATGATACG
GCCCTGAAGTCCCGGCTCAGCATCACCAGGGACACCTCCAAGAGGCAAGTCT
CCCTATCACTGAGCAGCGTGACGACTGAGGACACGGCCATGTACTTCTGTGC
AAGATCGGCATATAGTACTCTTTATGATTATGAGTATGCCGCTGATATCTACG
ACTGGGGCCCAGGACTCCTGGTCACCGTCTCCTCAACTAGTGGTGCGCCGGT
GCCGTATCCGGATCCGCTGGAACCGCGTGCCGCA (SEQ ID NO:5)

\>scFv#8
TCCTATGAACTGACCCAGCCGCCTTCAGTGTCGGTGGTTTGGGGNCNGANGG
CCGAGATCACCTGCCAGGGAGACCTACTGGATAAAAAATATACAGCTTGGTA
CCAGCAGAAGCCGGGCCAGGCTCCTATGAAAATCATTAATAAAGACAGTGAG
CGGCCTTCAGGGATCCGGGACCGGTTCTCGGGCTCCAGCTCAGGCAAAACAG
CCACCCTAACCATCAACGGGGCCCGGCCTGAGGACGAGGCCGACTATTACTG
TTTATCAGGTGACAGCAATAATAATGGTGTCTTCGGCAGCGGGACCAGCCTG
ACCGTCCTGGGTCAGCCCGCGGCCGCTGGTGGAGGCGGTTCAGGCGGAGGTG
GCTCTGGCGGTGGCGGATCGGCGCGCCAGGTGGAGCTGCAGGGGTCGGGAC
CCAGCCTGGTGAAGCCCTCGCAGACCCTCTCCCTCACCTGCACGGTCTCTGGA
TTCTCATGGCCCAACAATGCTGTGGATTGGGTCCGCCAGGCTCCAGGAAAGG
CGCCGGAGTGGCTTGGTGGTATTGCCGATAATGGAAGAACAAACTACAACAC
GGCCCTAAAAGCCCGGCTCAGCATCACTAGGGACACCGCCAAGAGCCATGTC
TCCCTATCGCTGAGCAGCGTGACAGCTGAGGATACGGCCGTTTACTATTGTAC
AGCGGGGGTTATGGTCATGCACGCCACTGACTACTGGGGCCCGGGACTCCTG
GTCACCGTCTCCTCAACTAGTGGTGCGCCGGTGCCGTATCCGGATCCGCTGGA
ACCGCGTGCCGCA (SEQ ID NO:7)

Fig. 1B

>scFv#21
CAGGCTGTGGTGACTCAGCCGTCCTCCGTGTCCGGGTCCCCGGGCCNNANAG
TCTCCATCACCTGCTCTGGAAGCAGCAGCAACGTTGGTAGATATGCTGTAGG
CTGGTTCCAACAGCTCCCAGGATCGGGCCTCAGAACCGTCATCTATTATAATA
GCAATCGACCCTCAGGGGTCCCCGACCGATTCTCTGGCTCCAAATCGGGCAA
CACAGCCACCCTGACCATCAGCTCGCTCCAGGCTGAGGATGAGGCCGATTAT
TTCTGTGGAAGTTATGACAGTAGTATCTATGGTGTTTTCGGCAGCGGGACCAG
GCTGACCGTCCTGGGTCAGCCCGCGGCCGCTGGTGGAGGCGGTTCAGGCGGA
GGTGGCTCTGGCGGTGGCGGATCGGCGCGCCAGGTGCAGCTGCAGGAGTCGG
GACCCAGCCTGGTGAGGCCCTCACAGACCCTCTCCCTCACCTGCACGATCTCT
GGATTCTCTTTAAGAGAGTATGGTGTAGGTTGGGTCCGCCAGGCTCCAGGAA
AGGGCGTTGGAGTGGCTTGGGCGAATAGATGATTCTGGATACACATTACATAA
TCCTGCCCTTAAGTCCCGGCTCACCATAACTAGGGACATCTCCAAGAGCCAA
GTCTCCCTGTCACTGAGCAGCGTGACACTTGAGGACACGGCCGAATATTACT
GCGTATATGCTAGTCGTGGTACTGCTTGGTTGGGAGACATCGATGTCTGGGGC
CCAGGACTCCTGCTCACTGTCTCCTCAACTAGTGGTGCGCCGGTGCCGTATCC
GGATCCGCTGGAACCGCGTGCCGCA (SEQ ID NO:9)

>scFv#E
CAGGCTGTGCTGACTCAGCCGTCCTCCGTGTCCAGGTCCCTGGGCCNNANTGT
CTCGATCACCTGCTCTGGAGGCAGCAGCAACGTTGGACAAGGTGATTATGTG
GCCTGGTTCCAACAGGTCCCAGGATCAGCCCCCAAACTCCTCATCTATGATGC
GACGAATCGAGCCTCGGGGGTCCCCGACCGATTCGTCGGCTCCAGATATGGC
AACTCAGCGACTCTGATCATCACCTCGGTCCAGGCTGAGGACGAGGCCGATT
ATTATTGTGCATCTTATGACAGTAGTATGTATACGATTTTCGGCAGCGGGACC
AGCCTGACCGTCCTGGGTCAGCCCGCGGCCGCTGGTGGAGGCGGTTCAGGCG
GAGGTGGCTCTGGCGGTGGCGGATCGGCGCGCCAGGTGGAGCTGCAGGGGTC
GGGACCCAGCCAGGTGAAGCCCTCACAGACCCTCTCCCTCATCTGCACGATC
TCTGGATTCTCATTAACCAGCAATAATGTAGCCTGGGTCCGCCAGGCTCCAGG
AAAGGGACTGGAGTGGGTTGGTGTCATAAGTGATGGTGGAACTCCATACTAT
AACTCGGCCCTGAAATCCCGGCTCAGCATCACCAGGGACACCTCCAAGAGCC
AGGTCTCCCTGTCACTGAGCAGCGTGACAACTGAGGACACGGCCGTGTACTA
CTGTGCACGGACGTTGGATTATAGTCATATTTGGTTGTACTCCGCCGACCAAT
GGGGCCCAGGACTCCTGGTCACCGTCTCCTCAACTAGTGGTGCGCCGGTGCC
GTATCCGGATCCGCTGGAACCGCGTGCCGCA (SEQ ID NO:11)

Fig. 1C

Anti-BoNT/A sheep scFv amino acid sequences

>scFv#2
QAVLTQPSSVSGSPGXXVSITCSGSRSNVGTYGVGWFQQLPGSGLRTIIYYNDKR
PSGVPDRFSASKSGNTATLIISSLQAEDEADYFCGSADGSSYGIFGSGTRLTVLGQ
PAAAGGGGSGGGGSGGGGSARQVGLQESGPSLVKPSQTLSLTCTVSGFSLSNSV
VGWVRQAPGKVPEWLGSIDSGGYTVADPALKSRLSITRDTSKSQVSLSLNSVTTE
DTAVYYCTRAYSITYYAYPPYIDYWGPGLLVTVSSTSGAPVPYPDPLEPRAA
(SEQ ID NO:2)

>scFv#3
QAVLTQPSSVSRSLGQSVSITCSGSSSNVGYGDYVGWFQRVPGSAPKLLIYGATT
RASGVPDRFSGSRSGNTATLTISSLQAEDEADYYCSSYDSSHYSIFGSGTSLTVLG
QPAAAGGGGSGGGGSGGGGSARQVELQESGPSLVKPSQTLSLTCTVSGFSLSSN
AVGWVRQAPGKAPEWVGGIDIDGRPVYKPGLKSRLSITRDTSNAQVSLSLSSVTT
EDTAVYFCASYYGGYLYNYAPGAYIEHLSPGLLITVSSTSGAPVPYPDPLEPRAA
(SEQ ID NO:4)

>scFv#7
SYELTQPPSMSVALGQTAKVTCQGDNLENFYVQWHQQKPGQAPVTVIFQDNKR
PSGIPDRFSGSNSGNTATLTISGARTEDEADYYCQSGHSSIGGVFGSGTSLTVLGQ
PAAAGGGGSGGGGSGGGGSARQVQLQESGPSLVKPSQTLSLTCTVSGFSLTGNS
VTWVRQAPGNVPEWLGGISRGGRTYYDTALKSRLSITRDTSKRQVSLSLSSVTTE
DTAMYFCARSAYSTLYDYEYAADIYDWGPGLLVTVSSTSGAPVPYPDPLEPRAA
(SEQ ID NO:6)

>scFv#8
SYELTQPPSVSVVWGXXAEITCQGDLLDKKYTAWYQQKPGQAPMKIINKDSERP
SGIRDRFSGSSSGKTATLTINGARPEDEADYYCLSGDSNNNGVFGSGTSLTVLGQ
PAAAGGGGSGGGGSGGGGSARQVELQGSGPSLVKPSQTLSLTCTVSGFSWPNNA
VDWVRQAPGKAPEWLGGIADNGRTNYNTALKARLSITRDTAKSHVSLSLSSVTA
EDTAVYYCTAGVMVMHATDYWGPGLLVTVSSTSGAPVPYPDPLEPRAA
(SEQ ID NO:8)

>scFv#21
QAVVTQPSSVSGSPGXXVSITCSGSSSSNVGRYAVGWFQQLPGSGLRTVIYYNSNR
PSGVPDRFSGSKSGNTATLTISSLQAEDEADYFCGSYDSSIYGVFGSGTRLTVLGQ
PAAAGGGGSGGGGSGGGGSARQVQLQESGPSLVRPSQTLSLTCTISGFSLREYGV
GWVRQAPGKALEWLGRIDDSGYTLHNPALKSRLTITRDISKSQVSLSLSSVTLED
TAEYYCVYASRGTAWLGDIDVWGPGLLLTVSSTSGAPVPYPDPLEPRAA (SEQ
ID NO:10)

Fig. 1D

>scFv#E
QAVLTQPSSVSRSLGXXVSITCSGGSSNVGQGDYVAWFQQVPGSAPKLLIYDAT
NRASGVPDRFVGSRYGNSATLIITSVQAEDEADYYCASYDSSMYTIFGSGTSLTV
LGQPAAAGGGGSGGGGSGGGGSARQVELQGSGPSQVKPSQTLSLICTISGFSLTS
NNVAWVRQAPGKGLEWVGVISDGGTPYYNSALKSRLSITRDTSKSQVSLSLSSV
TTEDTAVYYCARTLDYSHIWLYSADQWGPGLLVTVSSTSGAPVPYPDPLEPRAA
 (SEQ ID NO:12)

Fig. 1E

Nucleic acid sequence of scFv#7-2E is:

GGTGCGCCGGTGCCGTATCCGGATCCGCTCGAGCCGCGTGCCGGCTCCTATGAACTG
ACCCAGCCGCCTTCAATGTCGGTGGCCTTGGGACAGACGGCCAAGGTCACCTGCCAG
GGAGACAACTTAGAAAACTTTTATGTTCAGTGGCACCAGCAGAAGCCGGGCCAGGC
CCCTGTGACGGTCATTTTTCAGGATAATAAGAGGCCCTCGGGGATCCCTGACCGGTT
CTCTGGCTCCAACTCGGGGAACACGGCCACCCTGACCATCAGCGGGGCCCGGACCG
AGGACGAGGCCGACTATTACTGTCAGTCAGGCCACAGCAGTATCGGTGGTGTTTTCG
GCAGCGGGACCAGCCTGACCGTCCTGGGTCAGCCCGCGGCCGCTGGTGGAGGCGGT
TCAGGCGGAGGTGGCTCTGGCGGTGGCGGATCGGCGCGCCAGGTGCAGCTGCAGGA
GTCGGGACCCAGCCTGGTGAAGCCCTCACAGACCCTCTCCCTCACCTGCACGGTCTC
TGGCTTCTCATTAACGGGAAATTCTGTAACCTGGGTCCGCCAGGCTCCAGGAAACGT
GCCGGAGTGGCTTGGTGGTATAAGCCGCGGTGGACGCACATACTATGATACGGCCCT
GAAGTCCCGGCTCAGCATCACCAGGGACACCTCCAAGAGGCAAGTCTCCCTATCACT
GAGCAGCGTGACGACTGAGGACACGGCCATGTACTTCTGTGCAAGATCGGCATATA
GTACTCTTTATGATTATGAGTATGCCGCTGATATCTACGACTGGGGCCCAGGACTCC
TGGTCACCGTCTCCTCAACTAGTGGTGCGCCGGTGCCGTATCCGGATCCGCTGGAAC
CGCGTGCCGCA (SEQ ID NO: 13)

Amino acid sequence of scFv#7-2E is:

GAPVPYPDPLEPRAGSYELTQPPSMSVALGQTAKVTCQGDNLENFYVQWHQQKPGQAP
VTVIFQDNKRPSGIPDRFSGSNSGNTATLTISGARTEDEADYYCQSGHSSIGGVFGSGTSL
TVLGQPAAAGGGGSGGGGSGGGGSARQVQLQESGPSLVKPSQTLSLTCTVSGFSLTGNS
VTWVRQAPGNVPEWLGGISRGGRTYYDTALKSRLSITRDTSKRQVSLSLSSVTTEDTAM
YFCARSAYSTLYDYEYAADIYDWGPGLLVTVSSTSGAPVPYPDPLEPRAA
(SEQ ID NO:14)

Fig. 2

BoNT/A holotoxin binding VHHs:

JDA-D12
Nucleic acid sequence:

CAGGTGCAGCTCGTGGAGTCAGGAGGAGGCTTGGTGCAGCCTGGGGGATCTCTGAGACTCTCGTGTGTAGTCTCTGGAAGTGG
ACTTCAATACCTATATCATGGGCTGGTACCGCCAGGTTCCAGGGAAGCCGCGCGAGTTGGTCGCAGATATTACTACTGAAGGA
AAAACAAACTATGGGGCTCCGTAAAGGGAGGATTCACCATCTCCAGAGACAATGCCAAGAACACGGTGTATCTGCAAATGTTC
GGCCTGAAACCTGAGGACGCGGGGTAATTATGTCTGTAACGCAGACTGGAAGATGGGTGCATGGACGGCGGGGGACTACGGTA
TCGACTACTGGGGCAAAGCGACCCTGGTCACCGTCTCCTCAGAACCCAAGACACCAAAACCACAA (SEQ ID NO: 19)

Polypeptide sequence:

QVQLVESGGGLVQPGGSLRLSCVVSGSDFNTYIMGWYRQVPGKPRELVADITTEGKTNYGGSVKGRFTISRDNAKNTVYLQMFGLK
PEDAGNYVCNADWKMGAWTAGDYGIDYWGKGTLVTVSSEPKTPKPQ (SEQ ID NO: 20)

JDQ-A5
Nucleic acid sequence:

CAGGTGCAGCTCGTGGAGTCCGGGGTGGAGGCTTGGTGCAGCCTGGGGGGGTCTCTGAGACTCTCCTGTGCAGCCTCTGGAGGCA
ATCTGGATTATTATGCCATAGGCTGGTTCCGCCAGGCCCCAGGGAAGGAGCGCGAGGGGGTCTCATGTATTAGTAGTAGTGAT
GGTAGCACTGTCTATACAGACTCCGTGAAGGGCCGGATTCACCATCTCCAGAGACAATACCAAGAACACGGTAGATCTGCAAATG
GACAATTTGAAAGACACGGCCGTTTATTACTGTGCCACAGTCGTTAACTACTACACAGCCGGTGGGTCCATTCAC
GCGAGCCCGTATGAAATCTGGGGCCAGGGGACCCAGGTCACCGTCTCCTCAGCGCACCACAGCCAAGACCCCTCG (SEQ ID NO: 21)

Polypeptide sequence:

QVQLVESGGGLVQPGGSLRLSCAASAGNLDYYAIGWFRQAPGKEREGVSCISSSDGSTVYTDSVKGRFTISRDNTKNTVDLQMDNL
KPEDTAVYYCATVVNYYCTAGGSIHASPYEIWGQGTQVTVSSAHHSEDPS (SEQ ID NO: 22)

JDQ-B5
Nucleic acid sequence:

CAGGTGCAGCTCGTGGAGTCCGGCGGAGGCTTGGTGCACCCTGGGGGGTCTCTGAGACTCTCTTGTGCACCCTCTGCCAGTC
TACCCATCAACACCCTTCAACGCCCTTCAACAATATGGTGGGCTGGTACCGTCAGGCTCCAGGTAAACAGCGCGAAATGGTCGCA
AGTATTGGTCTACGGAATAAACTATGCAGACTCCGTGAAGGGCCGGATTCACCATCTCCAGAGACAACGCCAAGAACACGGTGGA
TCTGCAGATGGACAGCCTGCGACCTGAGGACTCAGCCAATACTACTGTCATAGAATACACCACTACTGGGGCAAAGGGA
CCCTGGTCACCGTCTCCTCGGAACCCAAGACACCAAAACCACAA (SEQ ID NO: 23)

Polypeptide sequence:

QVQLVESGGGLVHPGGSLRLSCAPSASLPSTPFNPFNNMVGWYRQAPGKQREMVASIGLRINYADSVKGRFTISRDNAKNTVDLQM
DSLRPEDSATYYCHEYTHYWGKGTLVTVSSEPKTPKPQ (SEQ ID NO: 24)

JDQ-C2
Nucleic acid sequence:

CAGGTGCAGCTCGTGGAGTCTGGTGGAGGCTTGGCCGCAGCCTGGGGGGGTCTCTGAGACTCTCCTGTGAAGCGTCTGGTTTTG
GGACATGGTTCAGGTTCGATGAGAACACCGTGAACTGGTACCGCCAGCCTCCAGGGAAAGTCGCGCGCGAGTTCGACGAGTTGGT
CGGCTCGTTACCCAAAAAGTGGCATCGGTAAGCTATTTAGACTCCGTGAAGGGCCCGATTCACGATCTCCAGAGACAACGCCAAAAA
AATGGCGTTCTGCAAATGGACAACCTGAAACCTGAGGACACGGCCGTCTATTATTGCAATGTCGGTGAATTTTGGGGCCAGG
GGACCCAGGTCACGATCTCCTCAGAACCCAAGACACCAAAACCACAA (SEQ ID NO: 25)

Polypeptide sequence:

QVQLVESGGGLAQPGGSLRLSCEASGFGTWFRFDENTVNWYRQPPGKSREFDELVARYPKSGIVTYLDSVKGRFTISRDNAKKMAF
LQMDNLKPEDTAVYYCNVGEFWGQGTQVTISSEPKTPKPQ (SEQ ID NO: 26)

Fig. 3A

JDQ-F12
Nucleic acid sequence:

CAGGTGCAGCTCGTGGAGTCGGGGGGAGGCTTGGTGCAGCCTGGGGGGTCTCTGAGACTCTCCTGTGCAGCCTCTGGATTCA
CCCTAGGGTCGCGGTTACATGAGCTGGGTCCGCCAGGCTCCAGGGAGAGGGGTTCGAGTGGGTCTCAAGTATTGAACCCTCTGG
TAGCGGCATGGGGATGGAGACTCCGCGAAGGGACGATTCACCACTTCCAGAGACGACGGCCAAGAACACGGCTTTATCTGCAAATGA
GCAACCTGCAACCCAGGACACGGCGGTGTTTATTACTGTGCAACAGGGTATCGGACGGGACGGAGGATTCCGGCTGGCTCGTG
GGGGCCAGGGGGACCCAGGTCACCGTCTCCTCAGAACCCAAGACACCAAAACCACAA (SEQ ID NO: 27)

Polypeptide sequence:

QVQLVESGGGLVQPGGSLRLSCAASGFTLGSRYMSWVRQAPGEGFEWVSSIEPSGTAWDGDSAKQRFTTSRDDAKNTLYLQMSN
LQPEDTGVYYCATGYRTDTRIPGGSWGQGTQVTVSSEPKTPKPQ (SEQ ID NO: 28)

JDQ-G8
Nucleic acid sequence:

CAGGTGCAGCTCGTGGAGTCTGGAGGAGGCTTGGTGCAGCCTGGGGGGTCTCTGAGACTCTCCTGTCAAGTCTCTGGATTCA
CCTTCGGTGACTGGGTCATGAGCTGGTTCCGCCAGGCTCCAGGGAAGGAGCGCGAATTCGTCGCAAGTATTACGGCTACTAG
TAGTCTAAAGTATTATGCAGACTCCGTGAAGGGCCGATTCACCATCTCCAGAGACAATGTCAACAACACACTGTTTCTGCAAATG
GATCGGCTGAAATCTGAGGACACGGCCGTTTATTACTGTCGGTCCCCCAACTACTGGGGCCAGGGGACCCAGGTCACCGTCTC
CGCCGAACCCAAGACACCAAAACCACAA (SEQ ID NO: 29)

Polypeptide sequence:

QVQLVESGGGLVQPGGSLRLSCQVSGFTFGDWVMSWFRQAPGKEREFVASITATSSLKYYADSVKGRFTISRDNVNNTLFLQMDRL
KSEDTAVYYCRSPNYWGQGTQVTVSAEPKTPKPQ (SEQ ID NO: 30)

JDQ-H7
Nucleic acid sequence:

CAGGTGCAGCTCGTGGAGTCAGGTGGAGGCTTGGTGCAGGTTGGGGGGTCTCTGAGACTCTCCTGTGTAGTTTCTGGAAGCG
ACATCAGTGGCATTGCGATGGGCTGGTACCGCCAGGCTCCAGGGAAGCGGCGCGAAATGGTCGCAGATATTTTTTCTGGCGG
TAGTACAGACTATGCAGGCTCCGTGAAGGGCCGATTCACCATCTGCAGAGACAACGCCAAGAAGACGGAGTATCTGCAAATGA
ACAACGTGAAACCTGAGGACACGGGAGTCTACTACTGTAGGCTGTACGGGAGCGGTGACTACTGGGGCCAGGGGACCCAGGT
CACCGTCTCCTCAGCGCACCACAGCGAAGACCCCTCG (SEQ ID NO: 31)

Polypeptide sequence:

QVQLVESGGGLVQVGGSLRLSCVVSGSDISGIAMGWYRQAPGKRREMVADIFSGGSTDYAGSVKGRFTISRDNAKKTSYLQMNNV
KPEDTGVYYCRLYGSGDYWGQGTQVTVSSAHHSEDPS (SEQ ID NO: 32)

Fig. 3B

BoNT/B toxoid binding VHHs:

JEQ-A5
Nucleic acid sequence:

CAGGTGCAGCTGGTGGAGTCAGGGGGAGGCTTGGTGCAGCCTGGGGGGTCTCTGAAACTCTCCTGTGCAGCCTCTGGATTCA
CTTTGGGACACCATCGCGTTGGCTGGTTCCGCCAGGCCCCAGGAAAGAAGCGGTGAGGGGGTCGCGTGTATTAGCGCCACTGG
TCTTAGCACACACTATTCAGACTCGGTGACCGGCCGATTTACCGTCTCCAGAGACAACCTCAACAACGTGGCGTATCTGCAGGT
GAACAGCCTGAAACCTGAGGACGCAGGTGTTTATTACTGTGCAAGCAGATTCTCGCCTTAATTCGGTCGATGCGAATATGTGCCT
TTCAGAGCCTCAGTATGACAACTGGGGCCAGGGGACCCAGGTCAGAATCTCCTCAGAACCCAAGACACCAAAACCACAA (SEQ
ID NO: 33)

Polypeptide sequence:

QVQLVESGGGLVQPGGSLKLSCAASGFTLGHHRVGWFRQAPGKKRGVACISATGLSTHYSDSVTGRFTVSRDNLNNVAYLQLNSL
KPEDAGVYYCASRFSLNSVDANMCLSEPQYDNWGQGTQVRISSEPKTPKPQ (SEQ ID NO: 34)

JEQ-H11
Nucleic acid sequence:

CAGGTGCAGCTGGTGGAGACGGGTGGAGGATTGGTGCAGGCCCGGGGGGCTCTCTGAGACTCTCCTGCGCAGGCTCTGGACGC
TCCTTCAGCGCCGCTGTCATGGGCTGGTTCCGGCCAGGCCGGCAGGGAAGGAGCGAGAATTCGGTAGCAGCACTTAGACAAATTAT
TGGTAGCACACACTATGCAGACTCGGTGAAGGGCCGGATTCAGCCATCTCCAGAGACAACGGCAAGAACATGTTGTATCTGGACAT
GAACAGCCTGAAACCTACGGACACGCGCGCGGTATTACTGCACAGCCGGGACCTCGGACTATGCTGGACGGTTTCTACGCGACCGG
GAGTATGACACCTGGGGTCAGGGGGGACTCAGGTCACCGTCTCCTCAGCGCACCACAGCGAAGACCCCTCG (SEQ ID NO: 35)

Polypeptide sequence:

QVQLVESGGGLVQAGGSLRLSCAGSGRSFSAAVMGWFRQAPGKEREFVAALRDIIGSTHYADSVKGRFTISRDNAKNMLYLDMNSL
KPTDTAAYYCTAGPPTMLDVSTDREYDTWGQGTQVTVSSAHHSEDPS (SEQ ID NO: 36)

Fig. 3C

JDQ-B5
Nucleic acid sequence:

CAGGTGCAGCTCGTGGAGTCCGGCGGAGGCTTGGTGCACCCTGGGGGGTCTCTGAGACTCTCTTGTGCACCCTCTGCCAGTC
TACCATCAACACCCTTCAACCCCTTCAACAATATGGTGGGCTGGTACCGTCAGGCTCCAGGGTAAACAGCGCGAAATGGTCGGCA
AGTATTGGTCTACGAATAAACTATGCAGACTCCGTGAAGGGCCGATTCACCATCTCCAGAGACAACGCCAAGAACACGGTGGA
TCTGCAGATGGACAGCCTGCGACCTGAGGAGTCAGCCACATACTACTGTCATATAGAATACACCCACTACTGGGGCGAAAGGGA
GCCCTGGTCACCGTCTCCTCGGAACCCAAGACACCAAAACCACAA (SEQ ID NO: 23)

Polypeptide sequence:

QVQLVESGGGLVHPGGSLRLSCAPSASLPSTPFNPFNNMVGWYRQAPGKQREMVASIGLRNYADSVKGRFTISRDNAKNTVDLQM
DSLRPEDSATYYCHIEYTHYWGKGTLVTVSSEPKTPKQEPKTPKQ (SEQ ID NO: 24)

JDQ-E9
Nucleic acid sequence:

CAGGTGCAGCTCGTGGAGTCCCGGAGGAGGCTTGGTGCGACCCTGGGGGGTCTCTGAGACTCTCTTGTGTAGTCTCTGGATTCG
CCTACGAAATGCCCATGATGGGCTGGTACCGGCCAGGCTCCAGGGGAATCAGGCGCGAGTTGGTCGCAACTATTGGTACAGGTGG
TAGGATGAACTATGCAGACTCCGTGAAGGGCCGATTCACCATCTCCAGAGACAACGCCAAGAACACGGTGTATCTGCAAATGA
ACAGCCTGAAACCTGAGGACACAGCCGCCTATTACTGTAAATCGAGTTTACAAATTACTGGGGCCAGGGGACCCAAGTCACC
GTCTCCTCAGAACCCAAGACACCAAAACCACAA (SEQ ID NO: 37)

Polypeptide sequence:

QVQLVESGGGLVRPGGSLRLSCVVSGFAYEMPMMGWYRQAPGNQRELVATIGTGGRMNYADSVKGRFTISRDNAKNTVYLQMNS
LKPEDTAAYYCKIEFTNYWGQGTQVTVSSEPKTPKQ (SEQ ID NO: 38)

JDQ-B9
Nucleic acid sequence:

CAGGTGCAGCTCGTGGAGTCAGGTGGAGGCTTGGTGCAGCCGGGGGGGATCTCTGAGACTGTCCTGTACAGTCTCTGGAAGCA
TCTTGGATCTACCTGGAATGAACTGGTATCGCCAGGCTCCAGGGGCCGCAGCGCGAGTTGGTCGCAGATATTAGTAGTGATGGT
AGGAGGACAAACTATGCAGACTCCGTGAAGGGCCGATTCACCATGTCCAGAGACAATGCCAAGAAAACGGTGTATCTGCAAAT
GGACAGCCTGAAACCTGACGACACGGCCGTCTATTACTGTAATGTGAAATTTACTCACCACTGGGGCCAGGGGATCCAGGGTCA
CCGTCTCCTCAGAACCCAAGACACCAAAACCACAA (SEQ ID NO: 39)

Polypeptide sequence:

QVQLVESGGGLVQPGGSLRLSCTVSGSIFDLPGMNWYRQAPGAQRELVADISSDGRRTNYADSVKGRFTMSRDNAKKTVYLQMDS
LKPDDTAVYYCNVKFTHHWGQGIQVTVSSEPKTPKQ (SEQ ID NO: 40)

Fig. 4A

JDQ-C5
Nucleic acid sequence:

CAGGTGCAGCTCGTGGAGTCAGGGGGAGGCTTGGTGCAGCCGGGGGGATCTCTGAGGCTGTCCTGTACGGTCTCTGGAAGC
ATCTTCGGCCTACCTGCATGAGCTGGTATCGCCAGGCTCCAGGGGCGCAGCGCGAGTTGGTCGCAGATATTAGTAGTGATG
GTGGGAGGACGCACTATGCAGACTCCGTGAAGGGCCGGCTTCACCATCTCCAGAGACAATGACAAGAAAACGGTGTATCTGCAG
ATGGACAGCCTGAAACCTGACGACACGGCCGTCTATTACTGTAATGTGAAATTTACTCACCACTGGGGCCAGGGGATCCAGGT
CACCGTCTCCTCAGAACCCAAGACACCAAAACCACAA (SEQ ID NO: 41)

Polypeptide sequence:

QVQLVESGGGLVQPGGSLRLSCTVSGSIFGLPCMSWYRQAPGAQRELVADISSDGGRTHYADSVKGRFTISRDNDKKTVYLQMDSL
KPDDTAVYYCNVKFTHHWGQGIQVTVSSEPKTPKPQ (SEQ ID NO: 42)

JDQ-F9
Nucleic acid sequence:

CAGGTGCAGCTCGTGGAGTCTGGGGGAGGCTTGGTGCAGGATGGGGGGTCTCTGAGGCTCTCCTGCACAACATCTGGAAGTA
TCGACAGTTTCAATGCCATAGAGTGGTACCGCCAGGCTCCAGGGAAGCAGCCGCGAATTGGTCGCAAGTATAAGTAGTGATGGT
CGTCGCACAAACTATGCAGACTCCGTGAAGGGCCGGATTCACCATCTCCGGAGACAACGCCAAGAACACGGTGTATCTGCAAAT
GAACAGCCTGAAACCTGAGGACACAGCCGTGTATTACTGTCATAGACCTTTTACCCACTACTGGGGCCAGGGGACCCAGGTCA
CCGTCTCCTCAGAACCCAAGACACCAAAACCACAA (SEQ ID NO: 43)

Polypeptide sequence:

QVQLVESGGGLVQDGGSLRLSCTTSGSIDSFNAIEWYRQAPGKQRELVASISSDGRRTNYADSVKGRFTISGDNAKNTVYLQMNSLK
PEDTAVYYCHRPFTHYNGQGTQVTVSSEPKTPKPQ (SEQ ID NO: 44)

Two nanobodies were identified that bind to BoNT/A holotoxin, H7 and B5. Each was expressed in different formats fused to E-tag and, in some cases, fused to one another H7/E and B5/E, single-tagged nanobody monomers H7/B5/E, single-tagged nanobody heterodimer E/H7/B5/E, double-tagged nanobody heterodimer ← E-tag
← nanobody

Fig. 6

Single-tagged nanobody heterodimer VHH potentially leads to decoration of toxin with two anti-tag mAbs

BoNT anti E-tag mAb

E-tag single-tagged heterodimer

Double-tagged nanobody heterodimer VHH potentially leads to decoration of toxin with four anti-tag mAbs anti E-tag mAb double-tagged heterodimer BoNT

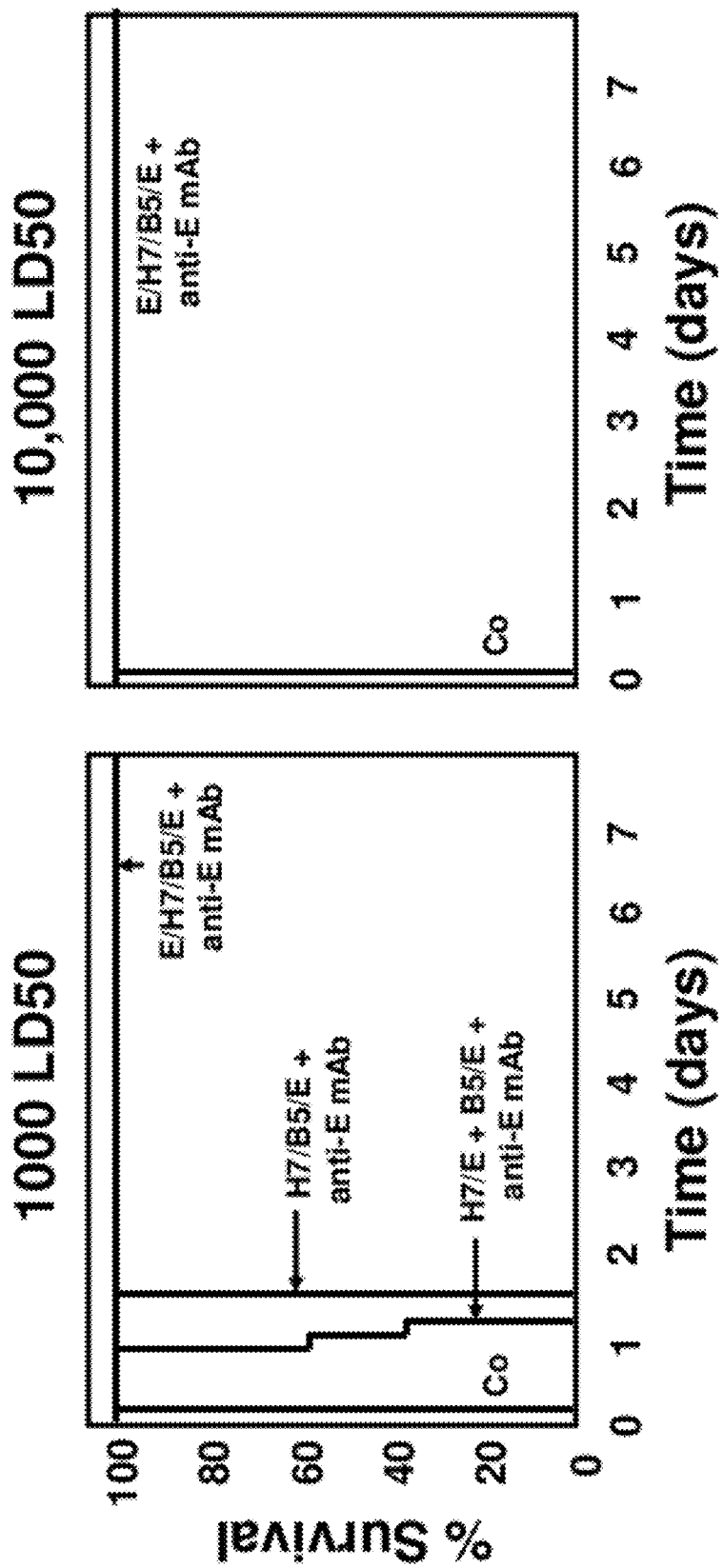

METHODS AND SYSTEMS FOR MULTI-ANTIBODY THERAPIES

RELATED APPLICATION

This application is a continuation-in-part of U.S. application Ser. No. 12/032,744, filed Feb. 18, 2008, which claims the benefit of U.S. Provisional Application No. 60/890,626, filed Feb. 20, 2007.

The entire teachings of the above applications are incorporated herein by reference.

GOVERNMENT SUPPORT

This invention was made with government support under grant AI030050 awarded by the National Institutes of Health. The government has certain rights in the invention.

BACKGROUND OF THE INVENTION

The production of antibodies and their storage is often a costly and lengthy process. In fact, development of a single antibody therapeutic agent can take years. Yet the use of multiple, different therapeutic antibodies are often necessary or desirable for the effective treatment of patients following a disease, outbreak or a bio-terrorist assault. The threat of a pandemic attack is real, and efforts to stockpile agents to combat such an outbreak have been attempted with some well underway. However, producing and stockpiling enough antibody to protect large populations is challenging. The shelf life of antibodies is often relatively short, and so antibodies have to be periodically replaced. As a result, developing and producing multiple antibodies that can bind to different targets (e.g. microbial and viral pathogens, toxins, cancer cells) for improved therapeutic effect is often a difficult task because it involves storing multiple antibodies for each pathogen or toxin.

Hence, a need exists for a cost effective and efficient way to provide antibody treatments to a large quantity of people. A further need exists for antibody therapeutics that are easier to develop and produce, and have a longer shelf life. Yet, a further need exists for antibody therapeutics that bind to multiple targets on the same disease agent, as well as different disease agents.

SUMMARY OF THE INVENTION

The methods of the present invention include methods for administering antibody therapeutic agents to treat one or more disease agents. The steps involve administering at least one binding agent, wherein the binding agent includes two or more monomers, each monomer has a binding region and the binding agent has one or more copies of a tag. The method also includes administering an anti-tag antibody (e.g., an anti-tag antibody), wherein the anti-tag antibody has an anti-tag region that is specific to the tag (e.g., to the one or more tags). The binding agent, each monomer of the binding agent, or combination thereof can further include one or more tags. The binding region of the monomer is specific to a portion of the disease agent. The monomer of the binding agent binds to a portion of the disease agent (e.g., the target) and the anti-tag antibody binds to the tag of the binding agent. Accordingly, the anti-tag antibody, which is directed to the disease agent by the binding agent, provides the effector activity that leads to a therapeutic effect. In fact, anti-tag antibody further embodies a polyclonal, antibody mixture, or an immunoglobulin such as IgA, IgD, IgE, IgG, or IgM. An embodiment of the methods includes administering a binding agent having two or more monomers, each having a binding region that binds to different portions of the disease agent, but each have the same tag or multiple copies of the same tag. The binding region of the binding agent can be an antibody fragment (e.g., a VHH (also called a nanobody)), a microprotein, peptide, a synthetic molecule, or an aptamer. The disease agent, in an embodiment, can be a virus, bacteria, cancer cell, parasite, or a molecule, protein or toxin produced therefrom. The tag can be an antibody epitope, including a polypeptide, sugar or DNA molecule. In the case of a polypeptide, the tag encompasses the epitope and generally includes between about 8 to about 15 amino acids (e.g., having an amino acid sequence of SEQ ID NO: 15).

The methods of the present invention further include methods of treating an individual having a viral infection, parasitic infection, bacterial infection, cancer, or a molecule, protein or toxin produced therefrom (e.g., a pathogenic molecule, protein, or toxin). The method relates to administering at least one binding agent (e.g., a monomer, a homodimer, a heterodimer, or a multimer), as described herein, and administering an anti-tag antibody, also as described herein. In an aspect, the present invention includes a heterodimer that has two monomers that are linked and each have a binding region that is specific to a different portion of the disease agent. The administration of one or more binding agents and/or the anti-tag antibody can occur at the same time or at different times (e.g., sequentially). The methods include reducing one or more symptoms associated with the viral infection, parasitic infection, bacterial infection, cancer or protein or toxin produced therefrom or from other sources such as snakes, insects, plants and other life forms.

The present invention further embodies an antibody therapeutic system or kit that has at least one binding agent having two or more monomers, and an anti-tag antibody, described herein.

Lastly, the present invention pertains to the binding agents described herein. The binding agent of the present invention includes, in an embodiment, more than one monomer that has a binding region and one or more copies of a tag, wherein the binding region binds with specificity (e.g., high specificity) to a portion of a disease agent. The binding region of the monomers can bind to the same portion of the disease agent (e.g. homodimers), or can bind to different portions of the disease agent (e.g. heterodimer). The binding agent can include one or more monomers (e.g., 1, 2, 3, 4, 5, 6, 7, 8, 9, 10, 15, 20, 25, 30, 35, 40, 45, 50, 60, 70, 80, 90, etc. monomers). The monomers can be attached directly or via a linker, as further described herein. The binding region of the monomers can be specific to the same disease agent or different disease agents. Each monomer can have a tag, or a tag can be shared by two or more monomers.

In an embodiment, the binding agent has more than one monomer that has a binding region and one or more copies of a tag, wherein the binding region is specific to a portion of a disease agent, wherein the monomer has one of the following amino acid sequences: an amino acid sequence encoded by a nucleic acid molecule having a sequence of SEQ ID NO: 1, 3, 5, 7, 9, 11, 13, 19, 21, 23, 25, 27, 29, 31, 33, 35, 37, 39, 41, 43, 45, 47, 49, 51, or combination thereof; an amino acid sequence encoded by a complement of SEQ ID NO 1, 3, 5, 7, 9, 11, 13, 19, 21, 23, 25, 27, 29, 31, 33, 35, 37, 39, 41, 43, 45, 47, 49, 51, or combination thereof; an amino acid sequence encoded by a nucleic acid molecule that hybridizes to SEQ ID NO: 1, 3, 5, 7, 9, 11, 13, 19, 21, 23, 25, 27, 29, 31, 33, 35, 37, 39, 41, 43, 45, 47, 49, 51, or combination thereof; or an amino acid sequence set forth in SEQ ID NO: 2, 4, 6, 8, 10, 12, 14, 20, 22, 24, 26, 28, 30, 32, 34, 36, 38, 40, 42, 44, 46, 48, 50, 52 or combination thereof. The binding agent can further include one or more polypeptide molecules having an amino acid sequence of SEQ ID NO: 15. In yet another aspect, the present invention includes a binding agent that has more than one monomer that has a binding region and one or more copies of a tag, wherein the binding region is specific to a portion of a disease agent, wherein the monomer is encoded by an isolated nucleic acid molecule having a sequence as follows: SEQ ID NO: 1, 3, 5, 7, 9, 11, 13, 19, 21, 23, 25, 27, 29, 31, 33, 35, 37, 39, 41, 43, 45, 47, 49, 51 or combination thereof; a complement of SEQ ID NO: 1, 3, 5, 7, 9, 11, 13, 19, 21, 23, 25, 27, 29, 31, 33, 35, 37, 39, 41, 43, 45, 47, 49, 51 or combination thereof; that hybridizes to SEQ ID NO: 1, 3, 5, 7, 9, 11, 13, 19, 21, 23, 25, 27, 29, 31, 33, 35, 37, 39, 41, 43, 45, 47, 49, 51 or combination thereof; or that encodes SEQ ID NO: 2, 4, 6, 8, 10, 12, 14, 20, 22, 24, 26, 28, 30, 32, 34, 36, 38, 40, 42, 44, 46, 48, 50, 52 or combination thereof.

The present invention also relates to isolated polypeptide and nucleic acid molecules relating to the binding agents specific to a botulism neurotoxin disease agent. Specifically, the present invention includes monomers with amino acid sequence encoded by a nucleic acid molecule having a sequence of SEQ ID NO: 19, 21, 23, 25, 27, 29, 31, 33, 35, 37, 39, 41, 43, 45, 47, 49, 51 or combination thereof; an amino acid sequence encoded by a complement of SEQ ID NO: 19, 21, 23, 25, 27, 29, 31, 33, 35, 37, 39, 41, 43, 45, 47, 49, 51 or combination thereof; an amino acid sequence encoded by a nucleic acid molecule that hybridizes to SEQ ID NO: 19, 21, 23, 25, 27, 29, 31, 33, 35, 37, 39, 41, 43, 45, 47, 49, 51 or combination thereof; and an amino acid sequence set forth in SEQ ID NO: 20, 22, 24, 26, 28, 30, 32, 34, 36, 38, 40, 42, 44, 46, 48, 50, 52 or combination thereof. Similarly, the present invention includes nucleic acid molecules having one of the following sequences: SEQ ID NO: 19, 21, 23, 25, 27, 29, 31, 33, 35, 37, 39, 41, 43, 45, 47, 49, 51 or combination thereof; a complement of SEQ ID NO: 19, 21, 23, 25, 27, 29, 31, 33, 35, 37, 39, 41, 43, 45, 47, 49, 51 or combination thereof; that hybridizes to SEQ ID NO:19, 21, 23, 25, 27, 29, 31, 33, 35, 37, 39, 41, 43, 45, 47, 49, 51 or combination thereof; and that encodes SEQ ID NO: 14, 20, 22, 24, 26, 28, 30, 32, 34, 36, 38, 40, 42, 44, 46, 48, 50, 52 or combination thereof. The present invention further includes binding agents having one or more copies of a tag with an amino acid sequence of SEQ ID NO: 15. Vectors, plasmids, or host cells having the nucleic acid molecules or that express the amino acid molecules of the present invention are further included herein. The present invention includes compositions that have the binding agents and an anti-tag antibody of the present invention and a physiologically acceptable carrier.

The present invention has a number of advantages. The systems and methods of the present invention allow for a more efficient system of treating disease agents and for storing quantities of antibodies for a large number of people. Binding agents of the present invention are compositions that can be stored for a longer period of time, as compared to antibodies with heavy and light chains. Binding agents are also generally easier to make than antibodies. The invention involves multiple (e.g., two or more) binding agents for use against multiple targets of the same disease, which often results in greater effectiveness. The binding agents in the system have the same tag, and an anti-tag antibody binds to all of the binding agents, even those that are specific to different portions of the disease agent. To make and store multiple antibodies for a number of targets is costly and inefficient, in comparison. Hence, a number of binding agents can more easily be stored, e.g., to protect against a potential biological threat, along with a single anti-tag antibody.

BRIEF DESCRIPTION OF THE DRAWINGS

FIGS. 1A-E show the nucleic acid sequences of scFv#2 (SEQ ID NO: 1), scFv#3 (SEQ ID NO: 3), scFv#7 (SEQ ID NO: 5), scFv#8 (SEQ ID NO: 7), scFv#21 (SEQ ID NO: 9), scFv#E (SEQ ID NO: 11), and amino acid sequences of scFv#2 (SEQ ID NO: 2), scFv#3 (SEQ ID NO: 4), scFv#7 (SEQ ID NO: 6), scFv#8 (SEQ ID NO: 8), scFv#21 (SEQ ID NO: 10), scFv#E (SEQ ID NO: 12).

FIG. 2 shows the nucleic acid sequence of scFv#7-2E (SEQ ID NO: 13) and amino acid sequence of scFv#7-2E (SEQ ID NO: 14).

FIGS. 3A-3C show the nucleic acid sequences of BoNT/A holotoxin binding VHHs including JDA-D12 (SEQ ID NO: 19), JDQ-A5 (SEQ ID NO: 21), JDQ-B5 (SEQ ID NO: 23), JDQ-C2 (SEQ ID NO: 25), JDQ-F12 (SEQ ID NO: 27), JDQ-G5 (SEQ ID NO: 29), JDQ-H7 (SEQ ID NO: 31), and BoNT/B holotoxin binding VHHs including JEQ-A5 (SEQ ID NO: 33), JEQ-H11 (SEQ ID NO: 35). The figures also show the corresponding amino acid sequences of BoNT/A holotoxin binding VHHs including JDA-D12 (SEQ ID NO: 20), JDQ-A5 (SEQ ID NO: 22), JDQ-B5 (SEQ ID NO: 24), JDQ-C2 (SEQ ID NO: 26), JDQ-F12 (SEQ ID NO: 28), JDQ-G5 (SEQ ID NO: 30), JDQ-H7 (SEQ ID NO: 32), and BoNT/B holotoxin binding VHHs including JEQ-A5 (SEQ ID NO: 34), JEQ-H11 (SEQ ID NO: 36).

FIGS. 4A-4B show the nucleic acid sequences of VHHs identified as BoNT/A binders that were experimentally shown to bind to the same epitope as JDQ-B5 (SEQ ID NO: 23), JDO-E9 (SEQ ID NO: 37), JDQ-B2 (SEQ ID NO: 39), JDQ-05 (SEQ ID NO: 41), and JDQ-F9 (SEQ ID NO: 43), along with the corresponding amino acid sequences JDQ-B5 (SEQ ID NO: 24), JDO-E9 (SEQ ID NO: 38), JDQ-B2 (SEQ ID NO: 40), JDQ-05 (SEQ ID NO: 42), and JDQ-F9 (SEQ ID NO: 44).

FIG. 5 is a schematic of a phylogenetic tree comparing the homology between BoNT/A binding VHHs within the JDQ-B5 competition group (compete for binding, thus bind the same epitope) in a comparison to random alpaca VHHs.

FIG. 6 shows a schematic of binding agents (here shown are VHH nanobodies) that are produced in different formats including formats in which the binding agents are fused to one or more E-tags and in some cases fused to one another.

FIG. 7 is a schematic showing a single-tagged binding agent (here shown are nanobody VHHs) produced as a heterodimer binding to the disease agent, a toxin, and leads to decoration of the toxin with two anti-tag monoclonal antibodies (mAbs).

FIG. 8 is a schematic showing a double-tagged binding agent (here shown are nanobody VHHs) produced as a heterodimer binding to the disease agent, a toxin, and leads to decoration of the toxin with four anti-tag mAbs.

FIG. 9A is a graph showing the percent (%) of mice surviving over a period of time (days) after receiving 1000 times the median lethal dose (LD50) of a *Botulinum* neurotoxin serotype A (BoNT/A) and the following binding agent combination: H7 and B5 VHH heterodimer with a single E-tag and an anti-E-tag mAb (H7/B5/E+anti-E mAb); H7 and B5 VHH monomers each with an E-tag and an anti-E-tag mAb (H7/E+B5/E+anti-E mAb); H7 and B5 VHH heterodimer with two E-tags and an anti-E-tag mAb (E/H7/B5/E+anti-E mAb) and a control (the toxin alone).

FIG. 9B is a graph showing the percent (%) of mice surviving over a period of time (days) after receiving the 10,000 times the LD50 of a *Botulinum* neurotoxin (BoNT) and H7 and B5 VHH heterodimer with two E-tags and an anti-E-tag mAb (E/H7/B5/E+anti-E mAb) and a control (the toxin alone). Remarkably, 100% of the mice survived a 10,000 LD50 challenge of BoNT/A when given only the double-tagged heterodimer and the anti-tag mAb.

Figure 10B:
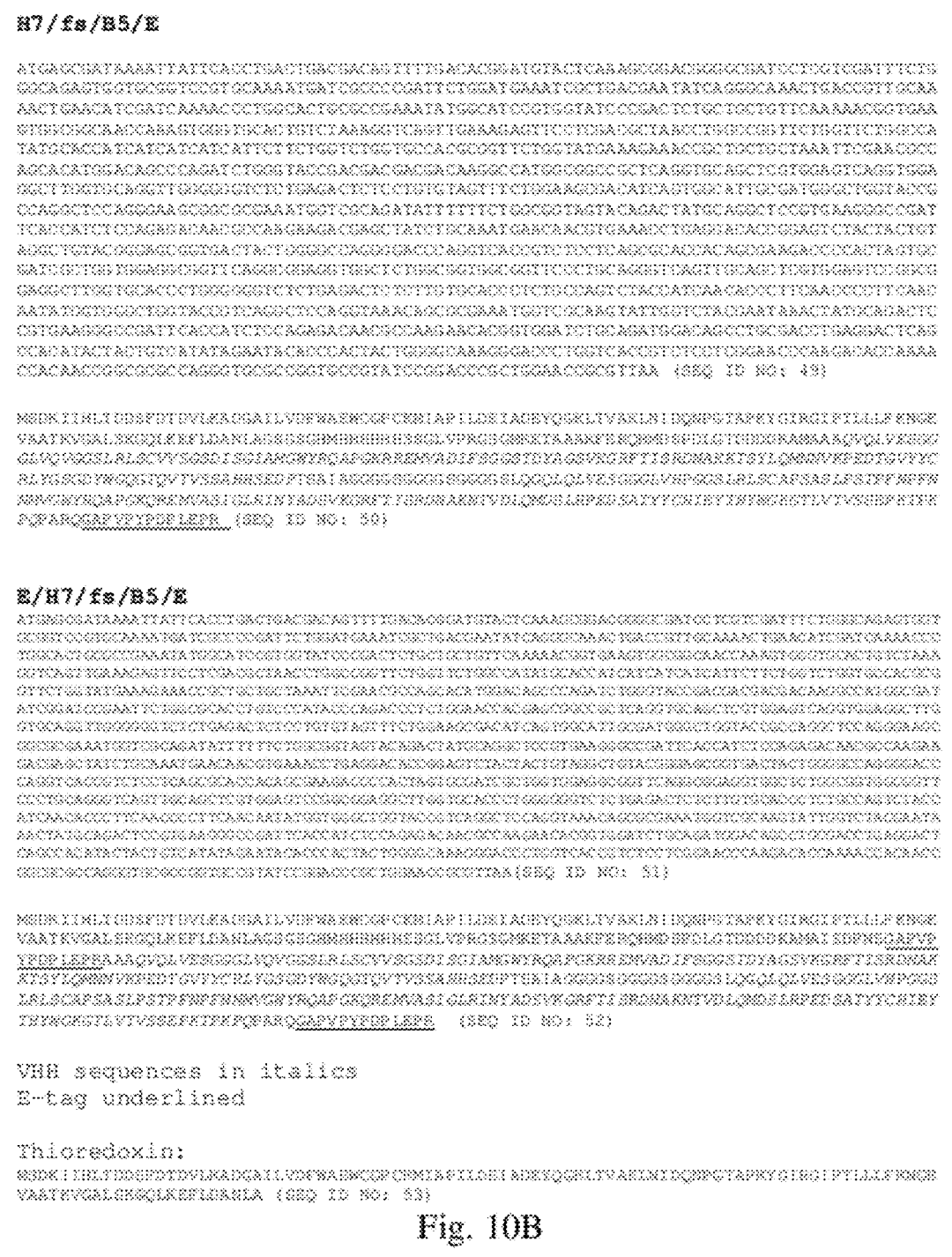

FIGS. 10A-10B show the recombinant nucleic acid sequences that include BoNT/A holotoxin binding VHHs such as thioredoxin/JDQ-H7(H7)/E-tag (SEQ ID NO: 45), thioredoxin/JDQ-B5(B5)/E-tag (SEQ ID NO: 47), thioredoxin/H7/flexible spacer (fs)/B5/E-tag (SEQ ID NO: 49), and thioredoxin/E-tag/H7/fs/B5/E-tag (SEQ ID NO: 51). The figures also show the corresponding amino acid sequences such as thioredoxin/H7/E-tag (SEQ ID NO: 46), thioredoxin/B5/E-tag (SEQ ID NO: 48), thioredoxin/H7/fs/B5/E-tag (SEQ ID NO: 50), thioredoxin/E-tag/H7/fs/B5/E-tag (SEQ ID NO: 52), and thioredoxin (SEQ ID NO: 53).

DETAILED DESCRIPTION OF THE INVENTION

The present invention relates to methods and systems that include one or more binding agents having a binding region and an epitopic tag; and an anti-tag antibody that binds the tag. The anti-tag antibody has a tag-specific binding region, also referred to as "anti-tag region." The methods of the present invention use, in an embodiment, two or more binding agents that are specific for different targets of the same disease agent, but have the same epitopic tag. Since the anti-tag antibody is specific for the tag, it can bind to each of the different binding agents. Additionally, in certain instances in which a single binding agent has more than one copy of the same tag, the overall efficacy of the antibody therapy increases.

Accordingly, in vivo, the binding agents bind to the disease agent (e.g., a polypeptide toxin produced by a bacterium). Using two or more binding agents has shown to be particularly effective in ridding the subject of the disease agent and improving symptoms caused by it. See Exemplification. The anti-tag antibody then binds to all of the binding agents, even binding agents that are specific for different portions of the disease agent. In the case in which the binding agents have multiple, identical tags, the anti-tag antibody has more available sites to which it can bind. As such, the anti-tag antibody allows for effector functions to occur (e.g., phagocytosis, neutralization, clearance of the disease agent), and in certain instances, an increase in the effector functions occurs when more than one copy of the tag is present on the binding agent. Binding agents are generally easier to make and have longer shelf-lives than antibodies. Rather than having multiple antibodies, which are more difficult to engineer and store, multiple binding agents along with a single anti-tag antibody can be used to treat individuals.

Binding Agent

The binding agent is a molecule that binds to a portion of a disease agent, and has a tag. The antibody therapeutic agents of the present invention allow the disease agent to be cleared, undergo phagocytosis, undergo neutralization, be inhibited, or otherwise mitigated by immune activity.

Binding agents include molecules such as antibody fragments (e.g., single chain antibodies, and nanobodies), microproteins (also referred to as cysteine knot proteins or knottins), darpins, anticalins, adnectins, peptide mimetic molecules, aptamers, synthetic molecules, and any molecule that binds to a disease agent and can elicit immune effector activity against the disease agent when the binding agent is bound by an anti-tag antibody. The binding agent, along with the anti-tag antibody, results in various effector functions such as phagocytosis and/or clearance, which is further described herein.

In certain embodiments, the binding agents can neutralize or inhibit the disease agent (e.g. prevent the disease agent entry into cells). In the case that the binding agents themselves are neutralizing, they can be advantageous in that they neutralize at the same time as triggering antibody mediated effector activity. In an example, a binding agent, referred to as scFvs (#2) in the Exemplification, is a neutralizing agent and it works well, as compared to similar neutralizing agents. However, in certain experiments performed in the exemplification, a neutralizing binding agent is not always necessary to protect mice from the toxin. Additionally, another factor is that the anti-tag antibody can increase the serum half-life of the binding agents.

In an aspect, the binding agent can be a monomer (e.g., a single unit) or comprise a number of monomers (e.g., a number of single units), such as a dimer, trimers, tetramers, pentamers, octamers, 20-mers, and/or multimers. In the case in which the binding agent is a monomer, the binding agent has one binding region that binds to an epitope of the disease agent. In the case of a multimer, the binding agent has two or more monomers with a binding region each of which binds to an epitope of a disease agent. The multimeric binding agent can comprise the same monomer, different monomers or a combination thereof. Accordingly, the multimers can be homogeneous (e.g., two or more monomers having a binding region that binds to the same site of a disease agent) or heterogeneous (e.g., two or more monomers having a binding region that binds to two or more different sites of one or more disease agents). As further described herein, the binding agent can have a single tag, multiple tags, or each monomer of the multimeric binding agent can have a tag. In an embodiment of a heterodimer used in the exemplification, the binding agent can have two tags (one per monomer) or share a tag. As shown in the figures and exemplification, a heterodimer having two E-tags has shown to remarkably protect infected animals from a single disease agent. The Exemplification shows multimers that were successfully tested and the data demonstrate that when a heterodimeric binding agent containing two tags along with the anti-tag antibody were administered, the same antitoxin efficacy can be achieved as with commercial antitoxins. Using this scaffold or multimeric binding agents and format, the commercial potential of these agents as antitoxins has dramatically improved. As multimeric binding agents work to specifically clear targeted molecules from the serum, the technology will prove effective in numerous other important therapeutic applications beyond antitoxins.

More particularly, FIG. 6 shows schematics of monomers and heterodimers that were made and exemplifies variations of the binding agent delivery format. In the first schematic, two monomers each having a tag were made. In the second schematic, a single-tagged heterodimer was made, and in the third schematic a double tagged heterodimer was made. FIG. 7 shows a toxin, BoNT, and two single tagged heterodimers binding to the toxin. The anti-tag monoclonal antibody (mAb) binds to the tag of the binding agent and promotes clearance of the complex. In this figure, the heterodimer leads to decoration of the toxin with two anti-tag mAbs. A double tagged heterodimer, shown in FIG. 8, binds to the toxin and the double tag allows for decoration of the toxin by four anti-tag mAbs. The format shown in FIG. 8 allows for an increase in the number of anti-tag mAbs, as compared to the format shown in FIG. 7, which should increase the clearance efficacy. The data described in FIG. 9A and in the Exemplification show that when mice are injected with 1000 times the median lethal dose of BoNT/A and treated simultaneously with various combinations of monomers and heterodimers containing a single tag or a double tag, and an anti-tag antibody—a protective effect is seen in all cases. The most striking effect is demonstrated by a double-tagged heterodimer comprising of the BoNT/A-binding VHHs, H7 and B5, and an anti-tag antibody. Even at 10,000 times the median lethal dose, a profound protective effect against the toxin is observed (FIG. 9B).

Binding Agents that Include Antibodies Fragments, Microproteins and Other Molecules that Bind the Disease Agent The term "antibody fragment" refers to portion of an immunoglobulin having specificity to the disease agent, or a molecule involved in the interaction or binding of the disease agent. The term, "antibody fragment", is intended to encompass fragments from both polyclonal and monoclonal antibodies including transgenically produced antibodies, single-chain antibodies (scFvs), recombinant Fabs, and recombinant camelid heavy-chain-only antibodies (VHHs). VHHs are also referred to as nanobodies.

Nanobodies are antibody-derived therapeutic proteins that contain the unique structural and functional properties of naturally-occurring heavy-chain antibodies. The Nanobody technology is based on fully functional antibodies from camelids that lack light chains. These heavy-chain antibodies contain a single variable domain (VHH) and two constant domains (CH2 and CH3). The cloned and isolated VHH domain is a stable polypeptide harboring the antigen-binding capacity of the original heavy-chain antibody. (Ablynx, Ghent, Belgium)

Suitable methods of producing or isolating antibody fragments of the requisite specificity are known in the art and include for example, methods which select recombinant antibody from a library, by PCR.

Functional fragments of antibodies, including fragments of chimeric, humanized, primatized, veneered or single chain antibodies, can also be produced. Functional fragments or portions of the foregoing antibodies include those which are reactive with the disease agent. For example, antibody fragments capable of binding to the disease agent or portion thereof, including, but not limited to scFvs, Fabs, VHHs, Fv, Fab, Fab' and F(ab')$_2$ are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain. Accordingly, the present invention encompasses a polynucleic acid that encodes the binding agent described herein (e.g., a binding fragment with a tag). In the case in which binding agents are made as part of a multimeric protein, the monomer or single binding agent (e.g., antibody fragments, microproteins, darpins, anticalins, adnectins, peptide mimetic molecules, aptamers, synthetic molecules, etc) can be linked. Any combination of binding agent types can be linked. In an embodiment, the monomer of a multimeric binding agent can be linked covalently. In another embodiment, a monomer binding agent can be modified, for example, by attachment (directly or indirectly (e.g., via a linker or spacer)) to another monomer binding agent. A monomer can be attached or genetically fused to another monomer e.g., by recombinant protein that is engineered to contain extra amino acid sequences that constitute the monomers. Thus, the DNA encoding one monomer is joined (in reading frame) with the DNA encoding the second monomer, and so on. Additional amino acids may be encoded between the monomers that produce an unstructured region separating the different monomers to better promote the independent folding of each monomer into its active conformation or shape. Commercially available techniques for fusing proteins can be used to link the monomers into a multimeric binding agent of the present invention.

Antagonist includes proteins or polypeptides that bind to the disease agent, inhibit function of the disease agent, and can form the binding region of the binding agent. Known antagonists, or those developed in the future, can be used with the present invention.

Binding agents include any molecule that binds to the disease agent including those that have scaffolds. Other examples of molecules include DARPins, Anticalins, and AdNectins. DARPins are derived from natural ankyrin repeat proteins and bind to proteins including e.g., human receptors, cytokines, kinases, human proteases, viruses and membrane proteins (Molecular Partners AG Zurich Switzerland). Anticalins are derived from lipocalins, and comprise a hypervariable loops supported by a conserved β-sheet framework, which acts as a binding agent. (Pieris AG, Germany). The scaffold for anticalins are lipocalins. AdNectins are derived from human fibronectin (e.g., the scaffold), and bind to targets of various medical conditions. (Adnexus, Waltham Mass.).

Binding Agents for *Botulinum* Neurotoxin (BoNT) Serotype A (BoNT/A) and Serotype B (BoNt/B)

Figure 5:
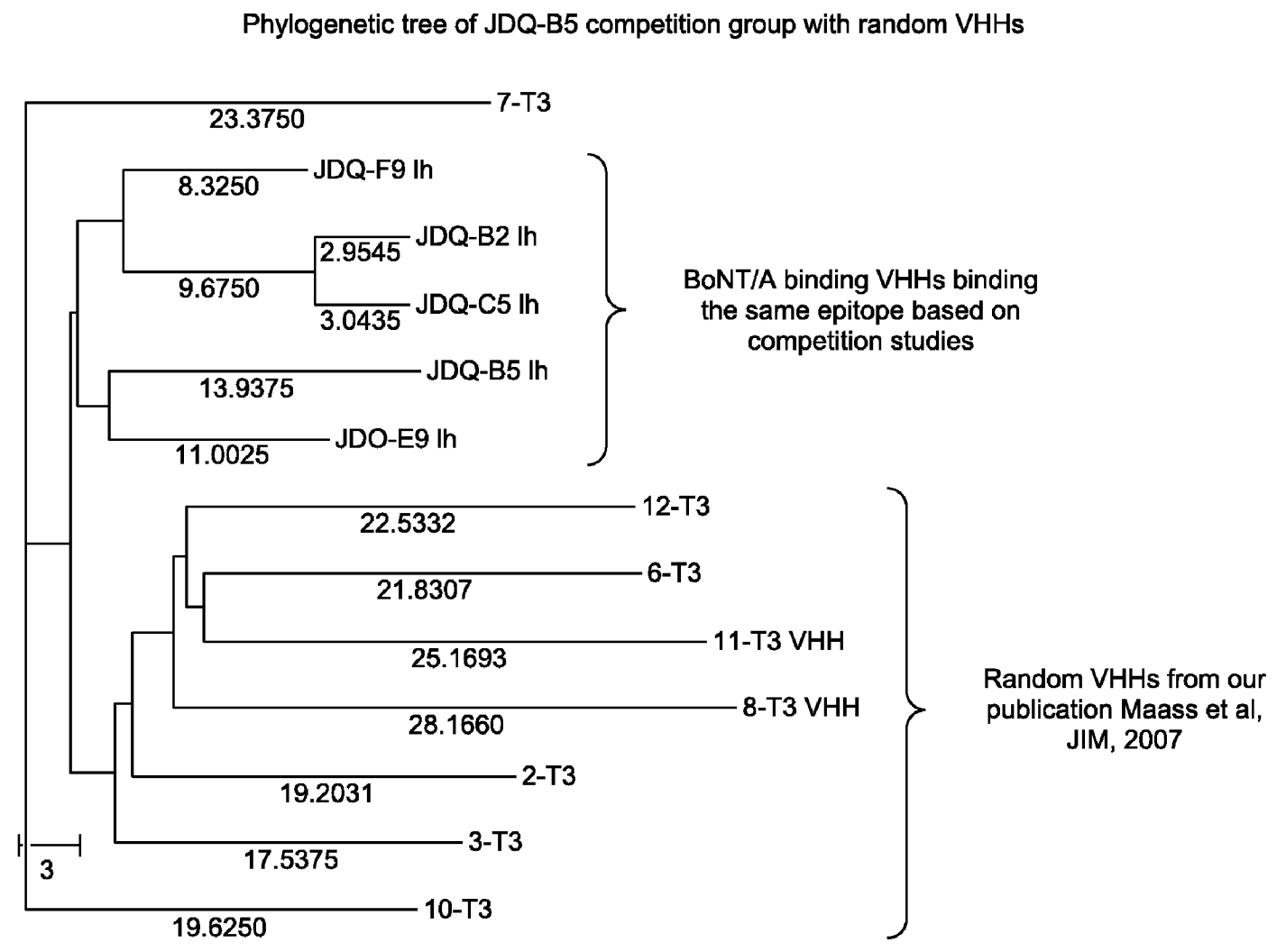

In particular, the present invention relates to binding agents that are specific to the microbial neurotoxin that causes botulism. There are at least seven different botulinum toxin serotypes (A to G), sometimes with various isotypes, and many of these different toxins can cause human disease. As described in the Exemplification section, several binding agents specific to botulinum neurotoxins, serotype A (BoNT/A) and serotype B (BoNT/A) were made. Hence, the methods and systems of the present invention include binding agents that have binding regions specific to one or more target areas of one or more neurotoxins involved with botulism. Sequences engineered to bind to this neurotoxin are shown in FIGS. 1, 3 and 4. Specifically, the present invention relates to binding agents having the amino acid sequence of SEQ ID NO: 2, 4, 6, 8, 10, 12, 14, 20, 22, 24, 26, 28, 30, 32, 34, 36, 38, 40, 42, 44, 46, 48, 50, 52 or combination thereof. Similarly, the present invention also includes binding agents that are encoded by a nucleic acid sequence of SEQ ID NO: 1, 3, 5, 7, 9, 11, 13, 19, 21, 23, 25, 27, 29, 31, 33, 35, 37, 39, 41, 43, 45, 47, 49, 51 or combination thereof. A tag was engineered and has amino acid sequence of SEQ ID NO: 15, and is genetically fused to the carboxyl end of these binding agents. FIG. 5 shows a phylogenetic tree of JDQ-B5 (SEQ ID NO: 24), a VHH binding agent specific to BoNT/A and other VHHs antibodies that compete with JDQ-B5 for binding to BoNT/A. The length of the branches in the tree represent the relatedness of the sequences with the shorter branches indicating greater relatedness (homology) and the longer branches having less homologous amino acid sequences.

The present invention embodies multiple binding agents, each to target different areas of one or more disease agents. In an embodiment, two or three binding agents specific to different targets of a disease agent can be used. In a case in which a number of disease agents can be involved in causing a disease or condition, such as botulism, multiple disease agents can be targeted. In the case of botulism, since any one of at least seven neurotoxin serotypes could be responsible, a pool of binding agents can be prepared that contain binding agents for all of the known serotypes that cause human disease. Botulism is often caused by exposure to a single BoNT serotype, but it is generally difficult to quickly determine which serotype is the cause. Thus, the standard of care in treating botulism includes administration of a number of antibodies to protect against most if not all of the serotypes that cause the disease in human. Hence, to protect against such a disease, an embodiment includes having or stockpiling binding agents that bind to several or preferably all of the serotypes that cause botulism. Certain studies have shown that effective antibody neutralization of a single BoNT serotype requires three different anti-BoNT monoclonal antibodies. Thus, to protect patients against all seven BoNT serotypes would require a pool of 21 different mAbs, a very formidable task. In contrast, preparation of a pool of small binding agents, each with a common tag, together with a single anti-tag mAb is a much more achievable task.

Additionally, the present invention encompasses multimeric binding agents having two or more monomers in which the monomer includes a VHH sequence recited herein. Accordingly, in an embodiment, a multimeric binding agent includes two or more of the VHH sequences described herein fused together. Any combination of two or more the VHH sequences can form a multimeric binding agent of the present invention. In a particular embodiment, the present invention relates to a heterodimer in which two different VHH sequences described herein are fused together.

Similarly, the targeted disease agents can be agents from different classes of pathogens. For example, a multi-target approach further includes binding agents that bind to viral disease agents, bacterial disease agents, parasite disease agents, cancer cells, proteins produced therefrom and any combination thereof.

Tags of Binding Agents

The binding agent is modified, for example, by incorporation of or attachment (directly or indirectly (e.g., via a linker)) of one or more tags. A tag is a molecule or antibody epitope that is attached or genetically fused to the binding agent and to which the anti-tag antibody binds. Genetic fusion refers to a recombinant protein that is engineered to contain extra amino acid sequences that constitute the tag. Thus, the DNA encoding the tag is joined (in reading frame) with the DNA encoding the binding agent. An embodiment of the invention includes more than one binding agents, with the same tag. Hence, in a system, the anti-tag antibody binds to all of the binding agents via the tag.

The tag can be attached to a portion of the binding agent so long as the tag does not interfere with the agent's ability to bind to the disease agent. The tag, for example, can be a polypeptide, sugar, or DNA molecule.

In an embodiment, the tag is incorporated by genetic fusion at the carboxyl end of the binding agent. The tag, itself, can also be a polypeptide joined at the amino terminal end or within the binding agent as long as the tag does not affect binding of the binding agent to the target and the tag remains accessible to the anti-tag mAb. The tag itself does not interact or bind with the disease agent. Preferably, the tag is an uncommon or unique molecule or peptide in nature. In an aspect, the tag is a polypeptide that ranges from about 5 amino acids to about 20 amino acids, and preferably between about 8 and about 15. In the exemplification, the tag used consisted of the following 13 amino acids: GAPVPYPDPLEPR (SEQ ID NO: 15). Examples of such tags also include c-myc and haemagglutinin protein, biotin, avidin, hapten (e.g., a carbohydrate or nucleotide) and the like.

The tag can be incorporated into the binding agent using recombinant technology in which the DNA encodes the binding agent genetically fused with the tag. Specifically, the coding sequence for the tag can be cloned into an expression vector and transfected into cells for recombinant expression.

Once the tag is incorporated into the binding agent, the binding agent, like an antibody, can be evaluated for its ability and affinity to bind to the disease agent.

Optionally, a linker or spacer can be used to attach the binding region of the binding agent with the tag. A linker can be used to indirectly attach a tag to the binding region. In one embodiment of the invention, the binding agent includes the binding region, a linker and a tag. The spacer/linker can be any compound, now known or later developed, that can attach the binding region with the tag.

Inclusion of more than one copy of the tag on a binding agent, in certain aspects, has additional advantages, such as by increasing the number of anti-tag antibodies that can bind to the binding agent. This would be the case, for example, where increasing the number of antibody Fc effector domains bound to the pathogenic protein through the tagged binding agent increased the therapeutic efficacy. Such an increase in efficacy is demonstrated and described in the Exemplification.

One or more tags can be attached to the binding agent. In the case of multimeric binding agents, they can have one tag, a single tag per monomer, or any number of tags (e.g., 1, 2, 3, 4, 5, 6, 7, 8, 9, 10, or more tags).

Disease Agent

The disease agent to which the binding agent binds can be any disease-causing target including those to be inhibited, or whose activity can be altered (e.g., neutralized, reduced or ceased), or that can be recognized by immune effectors and lead to clearance, opsonization, killing, etc. The disease agent can be a portion of a pathogen or a molecule released or secreted by the pathogen (e.g. toxin). A pathogen is an agent that causes a disease or condition, and includes a virus, cancer cell, bacterium, parasite or pathogenic protein. The disease agents include pathogenic proteins that are derived from normal cells, such as prions. Proteins or other molecules that are disease agents can be either independent of the pathogen or associated with or produced by a pathogen.

A virus is a microscopic particle that can infect the cells of a biological organism and replicate themselves in the host cell. With respect to the present invention, viral antigens, usually proteins, are targeted by the binding agent. Binding agents can be made to bind to such molecules on the virus, using the processes described herein. Example of viruses include Influenza, Rhinovirus, Rubeola, Rubella, Herpes, Smallpox, Chickenpox, Human Papilloma, Rabies, and Human Immunodeficiency viruses.

A parasite is an organism which lives on or in a different organism. Parasites have or express molecules that can be used as a target by the binding agent. Types of parasites include endoparasites (e.g., parasites that live inside the body of the host) and ectoparasites (e.g., parasites that live on the outside of the host's body). Examples of parasites include protozoans (e.g., plasmodium, cryptosporidium, microsporidia, and isospora), ticks, lice and parasitic worms.

Molecules on cancer cells can also be targets of the binding agent. In one embodiment, the target is a protein on the cancer cell or proteins that are characteristic to the cells of the cancer in question. Examples of proteins associated with cancer cells include CD33 (i.e., to a cytotoxic agent expressed in most leukemic blast cells), and the HER2/neu receptor for breast cancer.

Bacteria that can also be a target for the present invention include any bacteria including gram negative and gram positive bacteria. Examples of pathogenic bacteria belong to the genuses such as *Clostridium, Staphylococcus, Neisseria, Streptococcus, Moraxella, Listeria, Enterobacteriaceae, Escherichia coli, Corynebacterium, Klebsiella, Salmonella, Shigella, Proteus, Pseudomonas, Haemophilus, Bordetella, Legionella, Campylobacter, Helicobacter,* and *Bacteroides.* Methods for ascertaining the target are known in the art and will depend on the type of molecule being inhibited. For example, in the case where a class or group of bacteria are to be inhibited, conserved regions of a bacteria can be targeted, and binding agents that bind to these targets can be made. In other cases, if a specific bacterium is to be inhibited, then a non-conserved region of the bacteria can be targeted with the binding agents. The binding of the agents can be measured using standard assays, such as ELISAs, western blots and radioimmunoassays.

Pathogenic molecules including polypeptides or toxins are also disease agents to which binding agents can target. Pathogenic proteins refers to proteins that can cause, directly or indirectly, a disease, or condition in an individual. Proteins or toxins produced by bacteria, virus, or cancer cells are often such examples. In the Exemplification section, binding agents were made to a toxin produced by a *Clostridium* bacterium.

As shown in the Exemplification, using binding agents that target more than one area of the disease agent are shown more effective at protecting animals from the pathology of the disease agent, and symptoms caused by the disease agent are reduced or alleviated all together, as further described herein.

Anti-Tag Antibody

The anti-tag antibody is, in an embodiment, an antibody having an anti-tag region. The anti-tag region of the anti-tag antibody binds to the tag of each of the binding agents. Since the same tag is used for each of the binding agents, the anti-tag antibody essentially binds to the binding agents via the tag.

To generate an anti-tag antibody, processes known for making monoclonal antibodies, which are described herein, can be used. In the process of making monoclonal antibodies, for example, a mouse is injected with a disease agent along with an adjuvant. After a series of injections, the spleen of the mouse is removed, and the cells that make the antibody are fused with myeloma SP2/0 cells. The fused cells are grown and tested for their ability to make an antibody that binds to the disease agent, e.g., with ELISAs. To elicit an antibody that is specific to the tag, the tag, rather than the disease agent, is injected into the mouse during this process. Since the tags are generally small molecules (e.g. haptens) or peptides, they may need to be chemically coupled to a larger antigen for immunization or, if peptides, expressed as a genetic fusion to a larger protein, to make them more immunogenic. Humanized or chimeric antibodies can be made once the variable regions are determined.

Antibodies are already described herein, and can be used to carry out or facilitate effector functions. The anti-tag antibody further includes an immunoglobulin such as IgA, IgD, IgE, IgG, and IgM, including subtypes thereof. In addition to monoclonal antibodies, polyclonal antibodies specific to the tag can also be used with the present invention. Effector functions are generally carried out by the Fc portion of the immunoglobulin. Depending on the type of immunoglobulin chosen, the effector functions results in clearance of the disease agent (e.g., excretion, degradation, lysis or phagocytosis). Other molecules, now known or developed in the future, can be used as an anti-tag antibody so long as they bind to the tag and contain one or more of the antibody effector functions. For example, an anti-tag antibody may be an engineered protein consisting only of a domain that binds to the tag (e.g. an anti-tag scFv or VHH) fused to a minimal functional antibody Fc domain.

In mammals there are at least five types of antibody: IgA, IgD, IgE, IgG, and IgM, with 4 IgG and 2 IgA subtypes present in humans. These are classified according to differences in their heavy chain constant domains. Each immunoglobulin class differs in its biological properties. IgA can be found in areas containing mucus (e.g. in the gut, in the respiratory tract or in the urogenital tract) and prevents the colonization of mucosal areas by pathogens. IgD functions mainly as a disease agent receptor on B cells. IgE binds to allergens and triggers histamine release from mast cells and also provides protection against helminths (worms). IgG, in its four forms, provides the majority of antibody-based immunity against invading pathogens. IgM is expressed on the surface of B cells and also in a secreted form with very high affinity for eliminating pathogens in the early stages of B cell mediated immunity.

Some cells such as mast cells and phagocytes have specific receptors on their cell surface for binding antibodies. These are called Fc receptors and they interact with the Fc region of some antibodies (e.g. IgA, IgG, IgE). The engagement of a particular antibody with the Fc receptor on a particular cell will trigger the effector function of that cell. For example, phagocytes will phagocytose, and mast cells will degranulate. Effector functions generally result in destruction of the invading microbe. Hence, the type of immunoglobulin can be chosen depending on the type of effector function desired.

Methods and Systems of Administering Antibody Therapeutic Agents

The present invention includes methods of administering one or more binding agents including a multimeric binding agent and an anti-tag antibody, as described herein, to an individual. The binding agent can be administered as a monomer, or as a multimeric binding agent comprising more than one monomer. The methods involve administration of one or more multimeric binding agents that include monomers that each has a binding region that is specific to the disease agent. The binding agent also has one or more tags. The binding agents bind to the target region on the disease agent. Administration of two or more binding agents (e.g., monomer binding agents or multimeric binding agents), in an embodiment, increases the effectiveness of the antibody therapy, and better reduces the severity of one or more symptoms. The following combinations of binding agents can be administered: a single monomer, multiple (e.g., two or more) monomers, a multimeric binding agent comprising more than one monomer, multiple (e.g., two or more) multimeric binding agents comprising more than one monomer, or any combination thereof. Similarly, when the binding agents have more than one copy of the tag, an increase in efficacy occurs in certain embodiments. A single anti-tag antibody type binds to all binding agents with the tag. In the case in which the binding agents have multiple copies (e.g., two or more) of the same tag, the anti-tag antibody can bind to each copy of the tag on the binding agent. The phrase, "antibody therapeutic agents" or "antibody therapeutic preparation" refers to one or more compositions that include at least one binding agent and at least one anti-tag antibody, as described herein. The preparation can have additional elements including carriers, as described herein.

The administration of the one or more binding agents and/or anti-tag antibody can occur simultaneously or sequentially in time. The binding agents can be administered before, after or at the same time as another binding agent or the anti-tag antibody, so long as they are administered close enough in time to have the desired effect (e.g., before the binding agents have been cleared by the body). Thus, the term "co-administration" is used herein to mean that the binding agents and another binding agent or the anti-tag antibody will be administered at times to achieve treatment of the disease, or reduction in the level of the pathogen (e.g., virus, bacteria, cancer cell, proteins associated therewith, or combination thereof) and/or symptoms associated with it. The methods of the present invention are not limited to the sequence in which the binding agents and/or anti-tag antibody are administered; so long as the compositions are administered close enough in time to produce the desired effect. In an embodiment, the binding agents and/or anti-tag antibody can be premixed and administered together. The binding agents and/or anti-tag antibody can also be co-administered with other medications or compositions normally administered when treating the disease agent.

The methods of the present invention include treating a bacterial disease, a parasitic infection, viral diseases, cancer, molecules, proteins or toxins associated therewith. This is accomplished by administering the binding agents and anti-tag antibodies described herein to the infected individual. Administration ameliorates or reduces the severity of one or more the symptoms of the disease or condition. The presence, absence or severity of symptoms can be measured using tests and diagnostic procedures known in the art. Similarly the presence, absence and/or level of the disease agent can be measured using methods known in the art. Symptoms or levels of the disease agent can be measured at one or more time points (e.g., before, during and after treatment, or any combination thereof) during the course of treatment to determine if the treatment is effective. A decrease or no change in the level of the disease agent, or severity of symptoms associated therewith indicates that treatment is working, and an increase in the level of the disease agent, or severity of symptoms indicates that treatment is not working. Symptoms and levels of disease agents are measured using methods known in the art.

For example, where toxin is the disease agent, five mice per treatment group are injected intravenously or intraperitoneally with a lethal dose of toxin (10 LD50, 10× the dose that is lethal to 50% of the mice) and the binding agents to be tested are co-administered. The mice are regularly monitored for symptoms and survival. Symptoms that are monitored include difficulty breathing, lethargy, mobility, appetite and responsiveness. Toxin protection is assessed as increased survival and reduction of symptoms. The steps of the present invention led to a decrease or alleviation of the symptoms, and increase in survival. See Exemplification Section.

The antibody therapeutic agents including one or more binding agents and an anti-tag antibody can be administered in one or more pharmaceutical carriers. The terms "pharmaceutically acceptable carrier" or a "carrier" refer to any generally acceptable excipient or drug delivery device that is relatively inert and non-toxic. The binding agents and anti-tag antibody can be administered with or without a carrier. Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety. The binding agents and anti-tag antibody can be administered systemically or locally (e.g., by injection or diffusion).

Suitable carriers (e.g., pharmaceutical carriers) also include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation. A carrier (e.g., a pharmaceutically acceptable carrier) is preferred, but not necessary to administer one or more binding agents and an anti-tag antibody.

The binding agents and anti-tag antibody of the present invention can be administered intravenously, parenterally, orally, nasally, by inhalation, by implant, by injection, or by suppository. The composition can be administered in a single dose or in more than one dose over a period of time to confer the desired effect.

The actual effective amounts of compositions of the present invention can vary according to the binding agent being utilized, the particular composition formulated, the mode of administration and the age, weight and condition of the patient, for example. As used herein, an effective amount of the binding agents and anti-tag antibody is an amount which is capable of reducing one or more symptoms of the disease or conditions caused by the disease agent. Dosages for a particular patient can be determined by one of ordinary skill in the art using conventional considerations, (e.g. by means of an appropriate, conventional pharmacological protocol).

In another embodiment, a composition of the present invention can contain one or more of the DNA molecules of the present invention, either present as a mixture or in the form of a DNA molecule a multimer, DNA molecules each encoding a monomer, or any combination of molecules described herein, such that the polypeptide is generated in situ. In such compositions, the DNA can be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses the polypeptide on its cell surface. In a preferred embodiment, the DNA can be introduced using a viral expression system (e.g., vaccinia or other pox virus, retrovirus, or adenovirus), which can involve the use of a non-pathogenic (defective), replication competent virus. Techniques for incorporating DNA into such expression systems are well known to those of ordinary skill in the art. The DNA can also be "naked," as described, for example, in Ulmer et al., Science 259:1745-1749, 1993 and reviewed by Cohen, Science 259:1691-1692, 1993. The uptake of naked DNA can be increased by coating the DNA onto biodegradable beads, which are efficiently transported into the cells.

Systems or kits of the present invention include one or more binding agents having a binding region and one or more tags, and an anti-tag antibody having an anti-tag region (e.g., an anti-tag antibody), as described herein.

Polypeptides, Nucleic Acid Sequences, Vectors, Host Cells of the Binding Agents Engineered and Specific to a Botulism Neurotoxin The present invention relates to isolated polypeptide molecules that have been engineered or isolated to act as binding agents. In particular, the present invention includes polypeptide molecules that contain the sequence of any one of the binding agents (SEQ ID NO: 2, 4, 6, 8, 10, 12, 14, 20, 22, 24, 26, 28, 30, 32, 34, 36, 38, 40, 42, 44, 46, 48, 50, 52 or combinations thereof). See FIG. 1. The present invention also pertains to polypeptide molecules that are encoded by nucleic acid sequences, SEQ ID NO: 1, 3, 5, 7, 9, 11, 13, 19, 21, 23, 25, 27, 29, 31, 33, 35, 37, 39, 41, 43, 45, 47, 49, 51 or combinations thereof). A tag having the sequence set forth in SEQ ID NO:15 was used with these sequences-.

As used herein, the term "polypeptide" encompasses amino acid chains of any length, including full length proteins (i.e., disease agents), wherein the amino acid residues are linked by covalent peptide bonds. Thus, a polypeptide can comprise a portion of the binding agent, the entire binding agent, or it can contain additional sequences. The polypeptides of the binding agents of the present invention referred to herein as "isolated" are polypeptides that are separated away from other proteins and cellular material of their source of origin. The compositions and methods of the present invention also encompass variants of the above polypeptides and DNA molecules. A polypeptide "variant," as used herein, is a polypeptide that differs from the recited polypeptide only in conservative substitutions and/or modifications, such that the ability of the binding agent to bind to the disease agent target is retained.

The present invention also encompasses proteins and polypeptides, variants thereof, or those having amino acid sequences analogous to the amino acid sequences of binding agents described herein. Such polypeptides are defined herein as analogs (e.g., homologues), or mutants or derivatives. "Analogous" or "homologous" amino acid sequences refer to amino acid sequences with sufficient identity of any one of the amino acid sequences of the present invention so as to possess the biological activity (e.g., the ability to bind to the disease agent target). For example, an analog polypeptide can be produced with "silent" changes in the amino acid sequence wherein one, or more, amino acid residues differ from the amino acid residues of any one of the sequence, yet still possesses the function or biological activity of the polypeptide. In particular, the present invention relates to homologous polypeptide molecules having at least about 60% (e.g., 65%, 70%, 75%, 80%, 85%, 90% or 95%) identity or similarity with SEQ ID NO: 2, 4, 6, 8, 10, 12, 14, 20, 22, 24, 26, 28, 30, 32, 34, 36, 38, 40, 42, 44, 46, 48, 50, 52 or combination thereof. Percent "identity" refers to the amount of identical nucleotides or amino acids between two nucleotides or amino acid sequences, respectfully. As used herein, "percent similarity" refers to the amount of similar or conservative amino acids between two amino acid sequences.

Referring to FIGS. 4 and 5, when comparing the B5 (SEQ ID NO: 24) polypeptide sequence against the other polypeptide sequences in the chart, the polypeptide sequence similarity is as follows: E-9 (SEQ ID NO: 38) is 74% similar, C5 (SEQ ID NO: 42) is 67% similar, B2 (SEQ ID NO: 40) is 68% similar, and F9 (SEQ ID NO: 44) is 73% similar. The BLAST was done using default parameters on the NCBI website. Since these VHHs have shown to compete with B5, the present invention includes those sequences having a sequence similarity of at least about 65%. Similarly, when comparing the B5 (SEQ ID NO: 23) nucleic acid sequence against the other nucleic acid sequences in the chart, the polypeptide sequence similarity is as follows: E-9 (SEQ ID NO: 37) is 81% identical, C5 (SEQ ID NO: 41) is 75% identical, B2 (SEQ ID NO: 39) is 86% identical, and F9 (SEQ ID NO: 43) is 80% identical. The present invention includes those nucleic acid sequences having a sequence identity of at least 75%.

Homologous polypeptides can be determined using methods known to those of skill in the art. Initial homology searches can be performed at NCBI against the GenBank, EMBL and SwissProt databases using, for example, the BLAST network service. Altschuler, S. F., et al., J. Mol. Biol., 215:403 (1990), Altschuler, S. F., Nucleic Acids Res., 25:3389-3402 (1998). Computer analysis of nucleotide sequences can be performed using the MOTIFS and the FindPatterns subroutines of the Genetics Computing Group (GCG, version 8.0) software. Protein and/or nucleotide comparisons were performed according to Higgins and Sharp (Higgins, D. G. and Sharp, P. M., Gene, 73:237-244 (1988) e.g., using default parameters).

The present invention, in one embodiment, includes an isolated nucleic acid molecule having a sequence of SEQ ID NO: 1, 3, 5, 7, 9, 11, 13, 19, 21, 23, 25, 27, 29, 31, 33, 35, 37, 39, 41, 43, 45, 47, 49, 51 or combinations thereof. See FIGS. 1, 3 and 4. As used herein, the terms "DNA molecule" or "nucleic acid molecule" include both sense and anti-sense strands, cDNA, genomic DNA, recombinant DNA, RNA, and wholly or partially synthesized nucleic acid molecules. A nucleotide "variant" is a sequence that differs from the recited nucleotide sequence in having one or more nucleotide deletions, substitutions or additions. Such modifications can be readily introduced using standard mutagenesis techniques, such as oligonucleotide-directed site-specific mutagenesis as taught, for example, by Adelman et al. (DNA 2:183, 1983). Nucleotide variants can be naturally occurring allelic variants, or non-naturally occurring variants. Variant nucleotide sequences preferably exhibit at least about 70%, more preferably at least about 80% and most preferably at least about 90% homology to the recited sequence. Such variant nucleotide sequences will generally hybridize to the recited nucleotide sequence under stringent conditions. In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses isolated nucleic acid sequences that encode the binding agents and in particular, those which encode a polypeptide molecule having an amino acid sequence of SEQ ID NO: 2, 4, 6, 8, 10, 12, 14, 20, 22, 24, 26, 28, 30, 32, 34, 36, 38, 40, 42, 44, 46, 48, 50, 52 or combinations thereof.

As used herein, an "isolated" nucleotide sequence is a sequence that is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. The nucleic acid sequences of the binding agents of the present invention include homologous nucleic acid sequences. "Analogous" or "homologous" nucleic acid sequences refer to nucleic acid sequences with sufficient identity of any one of the nucleic acid sequences described herein, such that once encoded into polypeptides, they possess the biological activity of any one of the binding agents described herein. In particular, the present invention is directed to nucleic acid molecules having at least about 70% (e.g., 75%, 80%, 85%, 90% or 95%) identity with SEQ ID NO: 1, 3, 5, 7, 9, 11, 13, 19, 21, 23, 25, 27, 29, 31, 33, 35, 37, 39, 41, 43, 45, 47, 49, 51 or combinations thereof.

Also encompassed by the present invention are nucleic acid sequences, DNA or RNA, which are substantially complementary to the DNA sequences encoding the polypeptides of the present invention, and which specifically hybridize with their DNA sequences under conditions of stringency known to those of skill in the art. As defined herein, substantially complementary means that the nucleic acid need not reflect the exact sequence of the sequences, but must be sufficiently similar in sequence to permit hybridization with nucleic acid sequence under high stringency conditions. For example, non-complementary bases can be interspersed in a nucleotide sequence, or the sequences can be longer or shorter than the nucleic acid sequence, provided that the sequence has a sufficient number of bases complementary to the sequence to allow hybridization therewith. Conditions for stringency are described in e.g., Ausubel, F. M., et al., Current Protocols in Molecular Biology, (Current Protocol, 1994), and Brown, et al., Nature, 366:575 (1993); and further defined in conjunction with certain assays.

The invention also provides vectors, plasmids or viruses containing one or more of the nucleic acid molecules having the sequence of SEQ ID NO:1, 3, 5, 7, 9, 11, 13, 19, 21, 23, 25, 27, 29, 31, 33, 35, 37, 39, 41, 43, 45, 47, 49, 51 or combinations thereof). Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989).

Any of a variety of expression vectors known to those of ordinary skill in the art can be employed to express recombinant polypeptides of this invention. Expression can be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner can encode any of the polypeptides described herein including variants thereof.

Uses of plasmids, vectors or viruses containing the nucleic acids of the present invention include generation of mRNA or protein in vitro or in vivo.

In one embodiment, the present invention encompasses host cells transformed with the plasmids, vectors or viruses described above. Nucleic acid molecules can be inserted into a construct which can, optionally, replicate and/or integrate into a recombinant host cell, by known methods. The host cell can be a eukaryote or prokaryote and includes, for example, yeast (such as *Pichia pastorius* or *Saccharomyces cerevisiae*), bacteria (such as *E. coli*, or *Bacillus subtilis*), animal cells or tissue, insect Sf9 cells (such as baculoviruses infected SF9 cells) or mammalian cells (somatic or embryonic cells, Human Embryonic Kidney (HEK) cells, Chinese hamster ovary cells, HeLa cells, human 293 cells and monkey COS-7 cells). Host cells suitable in the present invention also include a mammalian cell, a bacterial cell, a yeast cell, an insect cell, and a plant cell.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a polypeptide. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example.

The host cell is then maintained under suitable conditions for expression and recovery of the polypeptides of the present invention. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria broth, Superbroth, Dulbecco's Modified Eagles Media (DMEM), RPMI-1640, M199 and Grace's insect media. The growth media can contain a buffer, the selection of which is not critical to the invention. The pH of the buffered Media can be selected and is generally one tolerated by or optimal for growth for the host cell.

The host cell is maintained under a suitable temperature and atmosphere. Alternatively, the host cell is aerobic and the host cell is maintained under atmospheric conditions or other suitable conditions for growth. The temperature should also be selected so that the host cell tolerates the process and can be for example, between about 13-40 degree Celsius.

A description of preferred embodiments of the invention follows.

EXEMPLIFICATION

Example 1

The concept is to improve therapies that involve multiple monoclonal antibodies (mAbs) by using small recombinant peptide, protein or polynucleotide agents that have the same binding specificity as the mAbs. Each of the recombinant binding agents is produced containing the same epitopic tag. A single mAb that recognizes the epitopic tag is co-administered to patients with the binding agents. The different agents bind to the same targets as the multiple mAbs and the anti-tag mAb binds to these agents through the epitopic tag. This permits delivery of the same therapeutic effect that is achieved with multiple mAb therapy, but requires only a single mAb. If desired, mAbs of different isotypes, or polyclonal anti-tag antibodies, could be used therapeutically to deliver different immune effector activities.

A number of small recombinant protein agents were generated. They were called single-chain Fvs (scFvs) and recognize botulinum neurotoxin serotype A (BoNT/A). These scFvs are essentially recombinant proteins that represent the antigen combining region of an immunoglobulin. Several anti-BoNT/A scFvs were produced and purified at laboratory scale. Each of the scFvs contains the amino acid sequence (GAPVPYPDPLEPR—SEQ ID NO: 15) near the carboxyl terminus which is an epitopic tag referred to herein as "E-tag." One of the scFvs (scFv#2) was shown to neutralize BoNT/A in a cell-based toxin assay (IC50~7 nM). A second scFv (scFv#7) had little or no neutralization activity in the assay, but was found to bind to BoNT/A with high affinity (Kd ~1 nM). The scFvs were tested for their ability to protect mice BoNT/A against intoxication following intravenous administration of the agents and toxin. The two scFvs were administered individually or together, and were given +/− a mouse anti-E-tag mAb by intravenous administration. Each mouse received 10 LD50s of BoNT/A, 5 mice per group. The results were as follows:

TABLE 1

Results from Experiment #1

| Agents Administered | Survival | Comments |
| --- | --- | --- |
| None | 0% | Death in less than a day |
| 20 ug scFv#2 | 0% | Death delayed about a day |
| 20 ug scFv#7 | 0% | Death delayed less than a day |
| 20 ug scFv#2 + 25 ug anti-E-tag mAb | 100% | Symptoms severe |
| 20 ug scFv#7 + 25 ug anti-E-tag mAb | 0% | Death delayed several days |
| 10 ug scFv#2 + 10 ug scFv#7 + 25 ug anti-E-tag mAb | 100% | No symptoms |

These results clearly show that a BoNT/A neutralizing scFv (scFv#2) does not significantly protect mice from the toxin unless it is accompanied by a mAb that recognizes an epitopic tag (E-tag) on the scFv. More importantly, combining this mAb with two scFvs, each with E-tag, dramatically improves the protective effect. In this case, the different scFv binding agents provide the additive effect and only the single anti E-tag mAb is needed.

A second study was performed using the same toxin challenge (10 LD50) and lower doses of the scFvs and the anti-E-tag mAb. In addition, two other non-neutralizing anti-BoNT/A scFvs (#3 and #21) were tested in combination with the neutralizing scFv#2. Whether the anti-E-tag mAb would function if administered at a different site and time than the toxin was also tested.

TABLE 2

Results from Experiment #2

| Agents Administered | Survival | Comments |
| --- | --- | --- |
| none | 0% | Death in about a day |
| 10 ug scFv#2 | 0% | Death delayed about 2 days |
| 10 ug scFv#2 + 10 ug anti-E-tag mAb (mAb administered intraperitoneally) | 100% | Symptoms moderate |
| 10 ug scFv#2 + 10 ug anti-E-tag mAb | 100% | Symptoms mild |
| 10 ug scFv#2 + 2 ug anti-E-tag mAb | 100% | Symptoms mild |
| 2 ug scFv#2 + 10 ug anti-E-tag mAb | 100% | Symptoms moderate |
| 5 ug scFv#2 + 3 ug scFv#7 + 10 ug anti-E-tag mAb | 100% | No symptoms |
| 1 ug scFv#2 + 1 ug scFv#7 + 10 ug anti-E-tag mAb | 100% | No symptoms |
| 5 ug scFv#2 + 4 ug scFv#3 + 10 ug anti-E-tag mAb | 100% | No symptoms |
| 5 ug scFv#2 + 3 ug scFv#21 + 10 ug anti-E-tag mAb | 100% | No symptoms |

These results entirely confirm those from the first experiment and extend them as follows. The mAb against the epitopic tag does not have to be pre-mixed with the scFv containing the epitopic tag to be effective (it can be administered at a different site and time). Combinations of two scFvs (each with E-tags) and the single anti-E-tag mAb, provide greater protection than with one scFv alone. This synergistic protective effect occurs using different scFvs and at significantly lower doses of the scFvs or mAb than used previously.

In the third experiment, we tested combinations of three and four scFvs with anti-tag mAb to protect against 100, 1000 and 10,000 LD50 doses of BoNT/A.

TABLE 3

Results from Experiment #3

| BoNT/A | Agents Administered All received 10/μg of anti-E-tag mAb | Survival | Comments |
| --- | --- | --- | --- |
| 100 LD50 | None | 0% | Death in less than a day |
| 100 LD50 | 2 μg scFv#2 + scFv#3 + scFv#21 | 100% | No symptoms |
| 1000 LD50 | None | 0% | Death in less than a day |
| 1000 LD50 | 2 μg scFv#2 + scFv#3 + scFv#21 | 100% | No symptoms |
| 1000 LD50 | 2 μg scFv#2 + scFv#3 + scFv#7 + scFv#21 | 100% | No symptoms |
| 10,000 LD50 | None | 0% | Death in a few hours |
| 10,000 LD50 | 2 μg scFv#2 + scFv#3 + scFv#21 | 0% | Death delayed one day |
| 10,000 LD50 | 2 μg scFv#2 + scFv#3 + scFv#7 + scFv#21 | 100% | Moderate symptoms |

The results clearly demonstrate the excellent potency of the tagged binding agent approach as antitoxins. Specifically, we find that we can completely protect mice against even mild symptoms of intoxication by 1000 LD50s using combinations of three or four scFvs with anti-E-tag mAb. We can protect mice against lethality from a 10,000 LD50 dose with a combination of four scFvs, although the mice did develop moderate symptoms. The ability to protect mice receiving up to 10,000 LD50s of BoNT/A is equivalent to the highest level of protection reported with pools of different anti-BoNT/A mAbs (Nowakowski et al, Proc Natl Acad Sci USA, 99:11346-50).

The next experiment tested whether a binding agent containing two copies of the epitopic tag would improve efficacy. To perform this experiment, the anti-BoNT/A binding agent, scFv#7, was engineered to contain another copy of the E-tag peptide. In all previous studies, the E-tag peptide was present on the carboxyl terminus of each scFvs. A new version of scFv#7 (called scFv#7-2E) was engineered, identical to scFv#7 except for an additional copy of the E-tag peptide fused to the amino terminus.

TABLE 4

Results from Experiment #4

| BoNT/A LD50 | Agents Administered All received 10/μg of anti-E-tag mAb | Survival | Comments |
|---|---|---|---|
| 100 | None | 0% | Death in less than 6 hours |
| 100 | 1 μg scFv#2 + scFv#3 + scFv#7 | 100% | No symptoms |
| 100 | 1 μg scFv#2 + scFv#3 + scFv#7-2E | 100% | No symptoms |
| 1000 | None | 0% | Death in less than 2 hours |
| 1000 | 1 μg scFv#2 + scFv#3 + scFv#7 | 0% | Death delayed 2 days |
| 1000 | 1 μg scFv#2 + scFv#3 + scFv#7-2E | 100% | No symptoms |
| 10,000 | None | 0% | Death in less than 2 hours |
| 10,000 | 1 μg scFv#2 + scFv#3 + scFv#7 | 0% | Death delayed less than a day |
| 10,000 | 1 μg scFv#2 + scFv#3 + scFv#7-2E | 20% | Death delayed many days |
| 10,000 | 1 μg scFv#2 + scFv#3 + scFv #21 + scFv#7 | 0% | Death delayed 2 days |
| 10,000 | 1 μg scFv#2 + scFv#3 + scFv #21 + scFv#7-2E | 100% | Moderate symptoms |

The results demonstrate that the binding agent with two epitope tags dramatically improved the in vivo antitoxin efficacy of the tagged binding agent. With a combination of three scFvs, including scFvs#2, scFvs#3 and scFvs#7 or scFvs#7-2E, clearly the use of scFvs#7-2E was substantially superior in protection of mice to the use of scFvs#7 with only one E-tag. This was particularly evident in the groups of mice challenged with 1000 LD50. In these groups, the triple combination of scFv#2+scFv#3+scFv#7 was insufficient to allow survival of the mice. When scFv#7 was replaced with scFv#7-2E, all the mice survived without symptoms. Furthermore, use of a pool of scFv#2+scFv#3+scFv#7-2E permitted the survival of one of five mice challenged with 10,000 LD50 and delayed the death of the other mice by several days. The equivalent pool with scFv#7 having only one E-tag only delayed death for one day in mice challenged with 10,000 LD50. Finally, an identical combination of four scFvs (#2, #3, #21 and #7) in which the efficacy using scFv#7 was compared with scFv#7-2E. With only one μg of each scFv, the use of scFv#7 did not permit survival of mice challenged with 10,000 LD50 while the same combination using scFv#7-2E was protective. The implication of these results is that it is possible to protect mice against high doses of toxin simply by administering a smaller number high affinity binding agents, each containing two or more epitope tags together with an anti-tag mAb.

The new approach improves therapeutic agent flexibility, permits the use of highly stable binding agents with long shelf life, substantially reduces the cost of production, and permits therapeutic applications that involve multiple target agents to be more commercially feasible. Furthermore, the new strategy will permit much more rapid development of new antitoxins. The binding agents should be much quicker to develop to commercialization than mAbs. The single anti-tag mAb needed for co-administration is the same for therapies requiring different tagged binding agents and thus can be preselected for its commercial scale up properties and stockpiled in advance of the development of the binding agents.

An immediate application is in anti-toxin therapy, an area of high interest because of bioterrorist threats. For example, it is now thought that effective prevention of botulinum intoxication using toxin neutralizing mAbs will require administration of three different mAbs each targeting the same toxin. Since there are at least seven different botulinum toxins, this suggests that 21 different mAbs (or more) may need to be stockpiled for use in the event of a major botulism outbreak as might occur through bioterror. Monoclonal antibodies are very expensive to produce and have relatively short shelf lives. This concept would make it possible to produce 21 different recombinant binding agents, each having longer shelf-life and lower production costs, and then stockpile only a single mAb. It is possible that this approach could open up many other mAb therapeutic strategies that involve multiple binding targets, but which have not been pursued because of prohibitive development and production costs and poor product shelf life. It also permits the use of mAbs of different antibody isotypes to be used with the same binding agents to provide greater therapeutic flexibility.

Example 2

BoNT/A VHH/Nanobody Binding Agents

VHH binding agents were identified, produced and purified that were specific to botulinum neurotoxin serotype A (BoNT/A) or serotype B (BoNT/B). All VHHs that were made have nine amino acids at the amino coding end that are determined by the forward PCR primer sequence. See FIGS. 3A-3C for the sequences. These sequences derive from 'framework 1' and can vary slightly from the original coding sequence. The most common sequence of these amino acids is QVQLVESGG (SEQ ID NO: 16) and this sequence is used for FIGS. 3A-C.

At the carboxyl coding end of all VHHs is either the short hinge sequence, AHHSEDPS (SEQ ID NO: 17), or the long hinge sequence, EPKTPKPQ (SEQ ID NO: 18). One or the other of these sequences are present in the VHHs sequence shown in FIGS. 3A-3C, and these appear interchangeable without loss of function. We know this because identical clones have been identified from alpacas that vary only in the hinge sequence and both retain virtually the same target binding function.

Variation within VHH Binding Agents:

During routine screening for VHH binding agents, different coding sequences are often identified that display significant homology as compared to randomly identified clones. When the VHH sequences are quite homologous, they are predicted to be related and thus to recognize the same epitope on the target to which they have been shown to bind. In some cases, this has been experimentally demonstrated using binding competition studies. These findings demonstrate that significant variation is permitted in VHH amino acid sequences without loss of target binding. An example of the extent of variation permitted is shown in FIGS. 4A-4B. Each of the VHHs identified in FIGS. 4A-4B as BoNT/A binders was experimentally shown to bind to the same epitope as JDQ-B5 based on binding competition studies.

FIG. 5 shows a phylogenetic tree that compares the homology between BoNT/A binding VHHs within the JDQ-B5 competition group to random alpaca VHHs. The homology comparison uses only the unique amino acids that are present between the forward PCR primer sequences and the hinge region (above). The distance of the lines is a measure of homology; the shorter the distance separating two VHHs, the more homologous. The four VHHs that bind to the same epitope as JDQ-B5 cluster within a group that is distinct from the random VHHs as shown. This is strong evidence that these clones are related. The results show that substantial variation in the VHH sequence is tolerated without loss of the target binding capability.

The coding DNAs for two different VHH monomers were cloned within an E. coli expression vector in several different ways so as to produce different recombinant proteins. To produce single VHH monomers, the VHH coding DNA was inserted into the plasmid pET32b such that the VHH is fused in frame with an amino terminal bacterial thioredoxin and a carboxyl terminal epitopic tag (E-tag GAPVPYPDPLEPR—SEQ ID NO: 15). Additional coding DNA deriving from the pET32b expression vector DNA was also present between the thioredoxin and VHH coding sequences, including DNA encoding six histidines (to facilitate purification) and an enterokinase cleavage site, DDDDK, (to permit enzymatic separation of thioredoxin from the VHH). The resulting expression vectors were used for the expression of VHH monomers. In particular, VHH monomers such as JDQ-H7 (SEQ ID NO: 32, referred to as "H7) and JDQ-B5 (SEQ ID NO: 24, referred to as "B5") were expressed in this system. A representation of the two monomer VHH proteins produced by these expression vectors, labeled as H7/E and B5/E, are shown in FIG. 10.

Similar expression vectors were prepared in pET32b in which DNA encoding two VHH monomers (e.g., SEQ ID NOs: 46 and 48) were present and joined in frame to yield heterodimers. For these constructions, the two VHHs were separated by DNA encoding 15 amino acids ((GGGGS)$_3$) SEQ ID NO: 54 that provides a flexible spacer (fs) between the expressed VHH proteins to separate the domains and facilitate independent folding. The E-tag coding DNA followed the second VHH coding DNA (e.g., SEQ ID NO: 49) in frame to permit expression of a single-tagged VHH heterodimer such as H7B5/E (SEQ ID NO: 50) in FIG. 10. In some cases a second copy of the E-tag coding DNA (e.g., SEQ ID NO: 51) was included upstream of the first VHH (at the amino coding end) for expression of a double-tagged VHH heterodimer such as E/H7/B5/E (SEQ ID NO: 52) in FIG. 10.

The thioredoxin fusion partner was included to improve expression and folding of the VHHs, but was not necessary for VHH function. The activity of the VHH agents to protect mice from BoNT/A intoxication in mouse lethality assays were tested using VHH agents in which thioredoxin was cleaved (by enterokinase) from the VHH and found that this caused no significant reduction in activity.

When administered to mice, a single-tagged heterodimer VHH is predicted to lead to decoration of the BoNT toxin by the anti E-Tag mAb in a ratio of 1:1. Accordingly, a single-tagged heterodimer should bind at two sites on the toxin and lead to decoration of the toxin with two anti E-tag antibodies (see FIG. 7). A double-tagged heterodimer provides for binding of the anti E-tag antibody in a ratio of 2:1 and thus should bind at two sites on the toxin and lead to decoration of the toxin with four anti-tag antibodies (see FIG. 8). These agents were tested for their ability to protect mice from intoxication by BoNT/A.

To do these studies, the VHH agents and the toxin are pre-mixed and then intravenously administered to groups of 5 mice. The mice are monitored and the time to death is noted for animals that succumb to the intoxication. In the results shown in FIG. 9A, a pool of two VHH monomers, H7/E and B5/E (1 µg each/mouse), in the presence of anti-E-tag mAb (Phadia, Sweden) (5 ug/mouse) only delayed death about a day in mice exposed to 1000 LD50 of BoNT/A. The single-tagged VHH heterodimer, H7/B5/E (2 µg/mouse) in the presence of anti-E-tag mAb (5 ug/mouse) delayed death about a day and a half in mice exposed to 1000 LD50 of BoNT/A. In contrast, the double-tagged heterodimer, E/H7/B5/E (2 µg/mouse) administered with anti-E-tag mAb permitted full survival of mice exposed to 1000 LD50 or even 10,000 LD50 of BoNT/A (FIG. 9B). Mice given the double-tagged VHH heterodimer, E/H7/B5/E, in the absence of co-administered anti-E-tag mAb, did not survive a 1000 LD50 dose of BoNT/E, showing that the anti-tag mAb was necessary for full efficacy. The ability of the double-tagged VHH heterodimer, E/H7/B5/E, administered with anti-E-tag mAb to protect mice against 10,000 LD50 demonstrates that this treatment achieves a level of efficacy similar to that obtained with commercial polyclonal antitoxin sera.

In other studies, the BoNT/A-binding VHH heterodimer agents were tested for their ability to prevent death in mice that were previously exposed to BoNT/A. In these studies, groups of five mice were first intoxicated with 10 LD50 BoNT/A. Then at 1.5 or 3 hours post-intoxication, some groups of mice were treated with the E/H7/B5/E heterodimer agent (2 µg/mouse) administered with anti-E-tag mAb (5 µg/mouse). Other groups of mice were given a dose of potent polyclonal anti-BoNT/A sera that had been prepared in sheep. This sera had been previously shown to protect mice against 10,000 LD50 of BoNT/A when it was co-administered with the toxin (studies performed as in previous paragraph). All mice were monitored and the time to death was determined for non-survivors. All ten control mice (2 groups) died within about a day. Five of five mice treated with polyclonal antisera 1.5 hour post-intoxication survived while four of five mice treated 3 hours post-intoxication survived. Five out of five mice treated with the VHH heterodimer and anti-E-tag mAb survived when treated both 1.5 hours and 3 hours post-intoxication. Thus the VHH heterodimer and anti-E-tag treatment was at least as effective as conventional polyclonal antitoxins at protecting mice from BoNT intoxication when administered in the more clinically relevant post-intoxication challenge model.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for enhancing clearance of a neurotoxin from a subject, the method comprising:
   administering to the subject a heterodimer binding agent comprising two monomers and two or more copies of a tag, wherein each of the monomers has a binding region, and the binding region of each monomer binds specifically to a different portion of the toxin; and
   administering to the subject an anti-tag antibody, wherein binding of the anti-tag antibody enhances the clearance of the toxin from the subject, and wherein at least one of the monomers is a VHH antibody having an amino acid sequence selected from the group consisting of:
   a. an amino acid sequence encoded by a nucleic acid molecule comprising a sequence of SEQ ID NO: 19, 21, 23, 25, 27, 29, 31, 33, 35, 37, 39, 41, 43, 45, 47, 49, 51 or a combination thereof; and
   b. an amino acid sequence set forth in SEQ ID NO: 20, 22, 24, 26, 28, 30, 32, 34, 36, 38, 40, 42, 44, 46, 48, 50, 52 or a combination thereof.

2. The method of claim 1, wherein the anti-tag antibody is a monoclonal antibody.

3. The method of claim 1, wherein the anti-tag antibody is a polyclonal antibody.

4. The method of claim 1, wherein the anti-tag antibody is selected from the group consisting of: IgA, IgD, IgE, IgG, and IgM.

5. The method of claim 1, wherein the heterodimer binding agent and the anti-tag antibody are administered sequentially.

6. The method of claim 1, wherein the heterodimer binding agent and the anti-tag antibody are administered simultaneously.

7. The method of claim 1, wherein the toxin is from a bacterium.

8. The method of claim 7, wherein the bacterium is a species of *Clostridium*.

9. The method of claim 8, wherein the bacterium is a species of gram positive bacterium.

10. The method of claim 9, wherein the species is *Clostridium botulinum*.

11. The method of claim 10, wherein the binding region is specific to a portion of *Botulinum* neurotoxin serotype A or serotype B.

12. The method of claim 3, wherein the heterodimer binding agent and the polyclonal anti-tag antibody are administered sequentially.

13. The method of claim 1, wherein administering the binding agent comprises contacting the subject with a nucleotide sequence encoding the binding agent.

14. The method of claim 1, wherein administering the anti-tag antibody comprises contacting the subject with a nucleotide sequence encoding the anti-tag antibody.

15. The method of claim 3, wherein the polyclonal antibody is produced by cells in the subject.

* * * * *

SEQUENCE LISTING

```
<160> NUMBER OF SEQ ID NOS: 54

<210> SEQ ID NO 1
<211> LENGTH: 816
<212> TYPE: DNA
<213> ORGANISM: Artificial Sequence
<220> FEATURE:
<223> OTHER INFORMATION: scFv#2 single chain antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 1
caggctgtgc tgactcagcc gtcctccgtg tccgggtccc cgggccnnan ggtctccatc      60
acctgctctg gaagcaggag taacgttggc acatatggtg taggttggtt ccaacagctc     120
ccaggatcgg cctcagaac catcatctat tataatgaca aacgaccctc aggggtcccc      180
gaccgattct ctgcctccaa atcgggcaac acagccaccc tgatcatcag ctcgctccag     240
gctgaggatg aggccgatta tttctgtgga agtgccgacg gtagtagtta tggtattttc     300
ggcagtggga ccagactgac cgtcctgggt cagcccgcgg ccgctggtgg aggcggttca     360
ggcggaggtg gctctggcgg tggcggatcg gcgcgccagg tggggctgca ggagtcggga     420
cccagcctgg tgaagccctc acagaccctc tccctcacct gcacgtctc tggattctca      480 ttgtccaaca gtgttgtagg ctgggtccgc caggctccag gaaaggtgcc ggagtggctt     540
ggtagtatag acagtggtgg ttacacagtc gctgacccgc ccctgaaatc ccgactcagc     600
atcacaaggg acacttccaa gagccaagtc tccctgtcac tgaacagcgt gacaactgag     660
gacacggccg tgtactactg tacaagggct tatagtatta cttattatgc gtatcccccc     720
tatatcgact actggggccc aggactcctg gtcaccgtct cctcaactag tggtgcgccg     780
gtgccgtatc cggatccgct ggaaccgcgt gccgca                                816

<210> SEQ ID NO 2
<211> LENGTH: 272
<212> TYPE: PRT
<213> ORGANISM: Artificial Sequence
<220> FEATURE:
<223> OTHER INFORMATION: scFv#2 single chain antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 2

Gln Ala Val Leu Thr Gln Pro Ser Ser Val Ser Gly Ser Pro Gly Xaa
1               5                   10                  15

Xaa Val Ser Ile Thr Cys Ser Gly Ser Arg Ser Asn Val Gly Thr Tyr
            20                  25                  30
```

```
Gly Val Gly Trp Phe Gln Gln Leu Pro Gly Ser Gly Leu Arg Thr Ile
         35                  40                  45
Ile Tyr Tyr Asn Asp Lys Arg Pro Ser Gly Val Pro Asp Arg Phe Ser
 50                  55                  60
Ala Ser Lys Ser Gly Asn Thr Ala Thr Leu Ile Ile Ser Ser Leu Gln
 65                  70                  75                  80
Ala Glu Asp Glu Ala Asp Tyr Phe Cys Gly Ser Ala Asp Gly Ser Ser
                 85                  90                  95
Tyr Gly Ile Phe Gly Ser Gly Thr Arg Leu Thr Val Leu Gly Gln Pro
            100                 105                 110
Ala Ala Ala Gly Gly Gly Ser Gly Gly Gly Ser Gly Gly Gly
            115                 120                 125
Gly Ser Ala Arg Gln Val Gly Leu Gln Glu Ser Gly Pro Ser Leu Val
130                 135                 140
Lys Pro Ser Gln Thr Leu Ser Leu Thr Cys Thr Val Ser Gly Phe Ser
145                 150                 155                 160
Leu Ser Asn Ser Val Val Gly Trp Val Arg Gln Ala Pro Gly Lys Val
                165                 170                 175
Pro Glu Trp Leu Gly Ser Ile Asp Ser Gly Gly Tyr Thr Val Ala Asp
            180                 185                 190
Pro Ala Leu Lys Ser Arg Leu Ser Ile Thr Arg Asp Thr Ser Lys Ser
            195                 200                 205
Gln Val Ser Leu Ser Leu Asn Ser Val Thr Thr Glu Asp Thr Ala Val
210                 215                 220
Tyr Tyr Cys Thr Arg Ala Tyr Ser Ile Thr Tyr Tyr Ala Tyr Pro Pro
225                 230                 235                 240
Tyr Ile Asp Tyr Trp Gly Pro Gly Leu Leu Val Thr Val Ser Ser Thr
                245                 250                 255
Ser Gly Ala Pro Val Pro Tyr Pro Asp Pro Leu Glu Pro Arg Ala Ala
            260                 265                 270

<210> SEQ ID NO 3
<211> LENGTH: 826
<212> TYPE: DNA
<213> ORGANISM: Artificial Sequence
<220> FEATURE:
<223> OTHER INFORMATION: scFv#3 Single Chain Antibody

<400> SEQUENCE: 3
caggctgtgc tgactcagcc gtcctccgtg tccaggtccc tgggccagag tgtctccatc      60
acctgctctg aagcagcag caacgttgga tatggtgatt atgtgggctg gttccaacgg     120
gtcccaggat cagcccccaa actcctcatc tatggtgcaa ccactcgagc tcgggggtc     180 cccgaccgat tctccggctc caggtctggc aacacagcga ctctgaccat cagctcgctc     240
caggctgagg acgaggccga ttattactgt tcatcttacg acagtagtca ctatagtatt     300
ttcggcagtg ggaccagcct gaccgtcctg ggtcagcccg cggccgctgg tggaggcggt     360
tcaggcggag gtggctctgg cggtggcgga tcggcgcgcc aggtggagct gcaggagtcg     420
ggacccagcc tggtgaagcc ctcacagacc ctctcccctca cctgcacggt ctctggattc     480
tcattaagta gcaatgctgt aggctgggtc cgccaggctc caggaaaggc gccggagtgg     540
gttggtggta tagatataga tggaaggccg gtctataaac caggcttaa gtcccggctc     600 agcatcacca gggacacctc caacgctcaa gtccctgt cactgagcag cgtgacaact     660
gaggacacgg ccgtgtactt ctgtgcaagt tattatggtg gttatcttta taattatgcc     720 cctgggggcat atatcgagca cttgagccca ggactcctga tcaccgtctc ctcaactagt     780
```

```
ggtgcgccgg tgccgtatcc ggatccgctg gaaaccgcgt gccgca              826
```

<210> SEQ ID NO 4
<211> LENGTH: 275
<212> TYPE: PRT
<213> ORGANISM: Artificial Sequence
<220> FEATURE:
<223> OTHER INFORMATION: scFv#3 single chain antibody

<400> SEQUENCE: 4

```
Gln Ala Val Leu Thr Gln Pro Ser Ser Val Ser Arg Ser Leu Gly Gln
1               5                   10                  15

Ser Val Ser Ile Thr Cys Ser Gly Ser Ser Asn Val Gly Tyr Gly
            20                  25                  30

Asp Tyr Val Gly Trp Phe Gln Arg Val Pro Gly Ser Ala Pro Lys Leu
        35                  40                  45

Leu Ile Tyr Gly Ala Thr Thr Arg Ala Ser Gly Val Pro Asp Arg Phe
    50                  55                  60

Ser Gly Ser Arg Ser Gly Asn Thr Ala Thr Leu Thr Ile Ser Ser Leu
65                  70                  75                  80

Gln Ala Glu Asp Glu Ala Asp Tyr Tyr Cys Ser Ser Tyr Asp Ser Ser
                85                  90                  95

His Tyr Ser Ile Phe Gly Ser Gly Thr Ser Leu Thr Val Leu Gly Gln
            100                 105                 110

Pro Ala Ala Gly Gly Gly Gly Ser Gly Gly Gly Ser Gly Gly
        115                 120                 125

Gly Gly Ser Ala Arg Gln Val Glu Leu Gln Glu Ser Gly Pro Ser Leu
130                 135                 140

Val Lys Pro Ser Gln Thr Leu Ser Leu Thr Cys Thr Val Ser Gly Phe
145                 150                 155                 160

Ser Leu Ser Ser Asn Ala Val Gly Trp Val Arg Gln Ala Pro Gly Lys
                165                 170                 175

Ala Pro Glu Trp Val Gly Gly Ile Asp Ile Asp Gly Arg Pro Val Tyr
            180                 185                 190

Lys Pro Gly Leu Lys Ser Arg Leu Ser Ile Thr Arg Asp Thr Ser Asn
        195                 200                 205

Ala Gln Val Ser Leu Ser Leu Ser Ser Val Thr Thr Glu Asp Thr Ala
    210                 215                 220

Val Tyr Phe Cys Ala Ser Tyr Tyr Gly Gly Tyr Leu Tyr Asn Tyr Ala
225                 230                 235                 240

Pro Gly Ala Tyr Ile Glu His Leu Ser Pro Gly Leu Leu Ile Thr Val
                245                 250                 255

Ser Ser Thr Ser Gly Ala Pro Val Pro Tyr Pro Asp Pro Leu Glu Pro
            260                 265                 270

Arg Ala Ala
        275
```

<210> SEQ ID NO 5
<211> LENGTH: 816
<212> TYPE: DNA
<213> ORGANISM: Artificial Sequence
<220> FEATURE:
<223> OTHER INFORMATION: scFv#7 Single Chain Antibody

<400> SEQUENCE: 5

```
tcctatgaac tgacccagcc gccttcaatg tcggtggcct gggacagac ggccaaggtc   60 acctgccagg gagacaactt agaaaacttt tatgttcagt ggcaccagca gaagccgggc  120
```

-continued

```
caggcccctg tgacggtcat ttttcaggat aataagaggc cctcggggat ccctgaccgg      180
ttctctggct ccaactcggg gaacacggcc accctgacca tcagcggggc ccggaccgag      240
gacgaggccg actattactg tcagtcaggc cacagcagta tcggtggtgt tttcggcagc      300
gggaccagcc tgaccgtcct gggtcagccc gcggccgctg gtggaggcgg ttcaggcgga      360
ggtggctctg gcggtggcgg atcggcgcgc caggtgcagc tgcaggagtc gggacccagc      420
ctggtgaagc cctcacagac cctctcccct acctgcacgg tctctggctt ctcattaacg      480
ggaaattctg taacctgggt ccgccaggct ccaggaaacg tgccgagtg gcttggtggt       540 ataagccgcg gtggacgcac atactatgat acggccctga gtcccggct cagcatcacc      600 agggacacct ccaagaggca agtctcccta tcactgagca gcgtgacgac tgaggacacg      660
gccatgtact tctgtgcaag atcggcatat agtactcttt atgattatga gtatgccgct      720
gatatctacg actggggccc aggactcctg gtcaccgtct cctcaactag tggtgcgccg      780
gtgccgtatc cggatccgct ggaaccgcgt gccgca                                816
```

<210> SEQ ID NO 6
<211> LENGTH: 272
<212> TYPE: PRT
<213> ORGANISM: Artificial Sequence
<220> FEATURE:
<223> OTHER INFORMATION: scFv#7 Single Chain Antibody

<400> SEQUENCE: 6

```
Ser Tyr Glu Leu Thr Gln Pro Pro Ser Met Ser Val Ala Leu Gly Gln
  1               5                  10                  15

Thr Ala Lys Val Thr Cys Gln Gly Asp Asn Leu Glu Asn Phe Tyr Val
             20                  25                  30

Gln Trp His Gln Gln Lys Pro Gly Gln Ala Pro Val Thr Val Ile Phe
         35                  40                  45

Gln Asp Asn Lys Arg Pro Ser Gly Ile Pro Asp Arg Phe Ser Gly Ser
     50                  55                  60

Asn Ser Gly Asn Thr Ala Thr Leu Thr Ile Ser Gly Ala Arg Thr Glu
 65                  70                  75                  80

Asp Glu Ala Asp Tyr Tyr Cys Gln Ser Gly His Ser Ser Ile Gly Gly
                 85                  90                  95

Val Phe Gly Ser Gly Thr Ser Leu Thr Val Leu Gly Gln Pro Ala Ala
            100                 105                 110

Ala Gly Gly Gly Gly Ser Gly Gly Gly Ser Gly Gly Gly Gly Ser
            115                 120                 125

Ala Arg Gln Val Gln Leu Gln Glu Ser Gly Pro Ser Leu Val Lys Pro
            130                 135                 140

Ser Gln Thr Leu Ser Leu Thr Cys Thr Val Ser Gly Phe Ser Leu Thr
145                 150                 155                 160

Gly Asn Ser Val Thr Trp Val Arg Gln Ala Pro Gly Asn Val Pro Glu
                165                 170                 175

Trp Leu Gly Gly Ile Ser Arg Gly Gly Arg Thr Tyr Tyr Asp Thr Ala
            180                 185                 190

Leu Lys Ser Arg Leu Ser Ile Thr Arg Asp Thr Ser Lys Arg Gln Val
            195                 200                 205

Ser Leu Ser Leu Ser Val Thr Thr Glu Asp Thr Ala Met Tyr Phe
            210                 215                 220

Cys Ala Arg Ser Ala Tyr Ser Thr Leu Tyr Asp Tyr Glu Tyr Ala Ala
225                 230                 235                 240
```

-continued

```
Asp Ile Tyr Asp Trp Gly Pro Gly Leu Leu Val Thr Val Ser Ser Thr
            245                 250                 255
Ser Gly Ala Pro Val Pro Tyr Pro Asp Pro Leu Glu Pro Arg Ala Ala
        260                 265                 270

<210> SEQ ID NO 7
<211> LENGTH: 795
<212> TYPE: DNA
<213> ORGANISM: Artificial Sequence
<220> FEATURE:
<223> OTHER INFORMATION: scFv#8 Single Chain Antibody
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 7
tcctatgaac tgacccagcc gccttcagtg tcggtggttt ggggncngan ggccgagatc      60
acctgccagg gagacctact ggataaaaaa tatacagctt ggtaccagca gaagccgggc     120
caggctccta tgaaaatcat taataaagac agtgagcggc cttcagggat ccggaccgg     180 ttctcgggct ccagctcagg caaaacagcc accctaacca tcaacggggc ccggcctgag    240
gacgaggccg actattactg tttatcaggt gacagcaata ataatggtgt cttcggcagc    300
gggaccagcc tgaccgtcct gggtcagccc gcggccgctg gtggaggcgg ttcaggcgga    360
ggtggctctg gcggtggcgg atcggcgcgc caggtggagc tgcaggggtc gggacccagc    420
ctggtgaagc cctcgcagac cctctcccct acctgcacgg tctctggatt ctcatggccc    480
aacaatgctg tggattgggt ccgccaggct ccaggaaagg cgccggagtg gcttggtggt    540
attgccgata atgaagaac aaactacaac acggccctaa agcccggct cagcatcact    600 agggacaccg ccaagagcca tgtctcccta tcgctgagca cgtgacagc tgaggatacg    660 gccgtttact attgtacagc gggggttatg gtcatgcacg ccactgacta ctggggcccg    720
ggactcctgg tcaccgtctc ctcaactagt ggtgcgccgg tgccgtatcc ggatccgctg    780
gaaccgcgtg ccgca                                                     795

<210> SEQ ID NO 8
<211> LENGTH: 265
<212> TYPE: PRT
<213> ORGANISM: Artificial Sequence
<220> FEATURE:
<223> OTHER INFORMATION: scFv#8 Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 8

Ser Tyr Glu Leu Thr Gln Pro Pro Ser Val Ser Val Val Trp Gly Xaa
1               5                   10                  15
Xaa Ala Glu Ile Thr Cys Gln Gly Asp Leu Leu Asp Lys Lys Tyr Thr
            20                  25                  30
Ala Trp Tyr Gln Gln Lys Pro Gly Gln Ala Pro Met Lys Ile Ile Asn
        35                  40                  45
Lys Asp Ser Glu Arg Pro Ser Gly Ile Arg Asp Arg Phe Ser Gly Ser
```

|    |     |     |     |     | 50  |     |     |     |     | 55  |     |     |     |     | 60  |     |     |     |
|----|-----|-----|-----|-----|-----|-----|-----|-----|-----|-----|-----|-----|-----|-----|-----|-----|-----|-----|

Ser Ser Gly Lys Thr Ala Thr Leu Thr Ile Asn Gly Ala Arg Pro Glu
65              70                  75                  80

Asp Glu Ala Asp Tyr Tyr Cys Leu Ser Gly Asp Ser Asn Asn Gly
                85                  90                  95

Val Phe Gly Ser Gly Thr Ser Leu Thr Val Leu Gly Gln Pro Ala Ala
            100                 105                 110

Ala Gly Gly Gly Ser Gly Gly Gly Ser Gly Gly Gly Ser
        115                 120                 125

Ala Arg Gln Val Glu Leu Gln Gly Ser Gly Pro Ser Leu Val Lys Pro
        130                 135                 140

Ser Gln Thr Leu Ser Leu Thr Cys Thr Val Ser Gly Phe Ser Trp Pro
145             150                 155                 160

Asn Asn Ala Val Asp Trp Val Arg Gln Ala Pro Gly Lys Ala Pro Glu
                165                 170                 175

Trp Leu Gly Gly Ile Ala Asp Asn Gly Arg Thr Asn Tyr Asn Thr Ala
            180                 185                 190

Leu Lys Ala Arg Leu Ser Ile Thr Arg Asp Thr Ala Lys Ser His Val
        195                 200                 205

Ser Leu Ser Leu Ser Ser Val Thr Ala Glu Asp Thr Ala Val Tyr Tyr
    210                 215                 220

Cys Thr Ala Gly Val Met Val Met His Ala Thr Asp Tyr Trp Gly Pro
225             230                 235                 240

Gly Leu Leu Val Thr Val Ser Ser Thr Ser Gly Ala Pro Val Pro Tyr
                245                 250                 255

Pro Asp Pro Leu Glu Pro Arg Ala Ala
            260                 265

<210> SEQ ID NO 9
<211> LENGTH: 810
<212> TYPE: DNA
<213> ORGANISM: Artificial Sequence
<220> FEATURE:
<223> OTHER INFORMATION: scFv#21 Single Chain Antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 9
caggctgtgg tgactcagcc gtcctccgtg tccgggtccc cgggccnnan agtctccatc      60
acctgctctg gaagcagcag caacgttggt agatatgctg taggctggtt ccaacagctc     120
ccaggatcgg gcctcagaac cgtcatctat tataatagca atcgaccctc agggtcccc     180 gaccgattct ctggctccaa atcgggcaac acagccaccc tgaccatcag ctcgctccag     240
gctgaggatg aggccgatta tttctgtgga agttatgaca gtagtatcta tggtgttttc     300
ggcagcggga ccaggctgac cgtcctgggt cagcccgcgg ccgctggtgg aggcggttca     360
ggcggaggtg gctctggcgg tggcggatcg gcgcgccagg tgcagctgca ggagtcggga     420
cccagcctgg tgaggccctc acagaccctc tccctcacct gcacgatctc tggattctct     480
ttaagagagt atggtgtagg ttgggtccgc caggctccag gaaaggcgtt ggagtggctt     540
gggcgaatag atgattctgg atacacatta cataatcctg cccttaagtc ccggctcacc     600
ataactaggg acatctccaa gagccaagtc tccctgtcac tgagcagcgt gacacttgag     660

```
gacacggccg aatattactg cgtatatgct agtcgtggta ctgcttggtt gggagacatc      720
gatgtctggg gcccaggact cctgctcact gtctcctcaa ctagtggtgc gccggtgccg      780
tatccggatc cgctggaacc gcgtgccgca                                       810
```

<210> SEQ ID NO 10
<211> LENGTH: 270
<212> TYPE: PRT
<213> ORGANISM: Artificial Sequence
<220> FEATURE:
<223> OTHER INFORMATION: scFv#21 Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 10

```
Gln Ala Val Val Thr Gln Pro Ser Ser Val Ser Gly Ser Pro Gly Xaa
1               5                   10                  15

Xaa Val Ser Ile Thr Cys Ser Gly Ser Ser Asn Val Gly Arg Tyr
            20                  25                  30

Ala Val Gly Trp Phe Gln Gln Leu Pro Gly Ser Gly Leu Arg Thr Val
        35                  40                  45

Ile Tyr Tyr Asn Ser Asn Arg Pro Ser Gly Val Pro Asp Arg Phe Ser
    50                  55                  60

Gly Ser Lys Ser Gly Asn Thr Ala Thr Leu Thr Ile Ser Ser Leu Gln
65                  70                  75                  80

Ala Glu Asp Glu Ala Asp Tyr Phe Cys Gly Ser Tyr Asp Ser Ser Ile
                85                  90                  95

Tyr Gly Val Phe Gly Ser Gly Thr Arg Leu Thr Val Leu Gly Gln Pro
            100                 105                 110

Ala Ala Ala Gly Gly Gly Gly Ser Gly Gly Gly Ser Gly Gly Gly
        115                 120                 125

Gly Ser Ala Arg Gln Val Gln Leu Gln Glu Ser Gly Pro Ser Leu Val
130                 135                 140

Arg Pro Ser Gln Thr Leu Ser Leu Thr Cys Thr Ile Ser Gly Phe Ser
145                 150                 155                 160

Leu Arg Glu Tyr Gly Val Gly Trp Val Arg Gln Ala Pro Gly Lys Ala
                165                 170                 175

Leu Glu Trp Leu Gly Arg Ile Asp Asp Ser Gly Tyr Thr Leu His Asn
            180                 185                 190

Pro Ala Leu Lys Ser Arg Leu Thr Ile Thr Arg Asp Ile Ser Lys Ser
        195                 200                 205

Gln Val Ser Leu Ser Leu Ser Ser Val Thr Leu Glu Asp Thr Ala Glu
    210                 215                 220

Tyr Tyr Cys Val Tyr Ala Ser Arg Gly Thr Ala Trp Leu Gly Asp Ile
225                 230                 235                 240

Asp Val Trp Gly Pro Gly Leu Leu Leu Thr Val Ser Ser Thr Ser Gly
                245                 250                 255

Ala Pro Val Pro Tyr Pro Asp Pro Leu Glu Pro Arg Ala Ala
            260                 265                 270
```

<210> SEQ ID NO 11
<211> LENGTH: 816
<212> TYPE: DNA
<213> ORGANISM: Artificial Sequence
<220> FEATURE:
<223> OTHER INFORMATION: scFv#E Single Chain Antibody
<220> FEATURE:

```
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 11
caggctgtgc tgactcagcc gtcctccgtg tccaggtccc tgggccnnan tgtctcgatc      60
acctgctctg gaggcagcag caacgttgga caaggtgatt atgtggcctg gttccaacag     120
gtcccaggat cagcccccaa actcctcatc tatgatgcga cgaatcgagc ctcgggggtc     180
cccgaccgat tcgtcggctc cagatatggc aactcagcga ctctgatcat cacctcggtc     240
caggctgagg acgaggccga ttattattgt gcatcttatg acagtagtat gtatacgatt     300
ttcggcagcg ggaccagcct gaccgtcctg ggtcagcccg cggccgctgg tggaggcggt     360
tcaggcggag gtggctctgg cggtggcgga tcggcgcgcc aggtggagct gcaggggtcg     420
ggacccagcc aggtgaagcc ctcacagacc ctctccctca tctgcacgat ctctggattc     480
tcattaacca gcaataatgt agcctgggtc cgccaggctc caggaaaggg actggagtgg     540
gttggtgtca agtgatgg tggaactcca tactataact cggccctgaa atcccggctc     600
agcatcacca gggacacctc caagagccag gtctccctgt cactgagcag cgtgacaact     660
gaggacacgg ccgtgtacta ctgtgcacgg acgttggatt atagtcatat ttggttgtac     720
tccgccgacc aatggggccc aggactcctg gtcaccgtct cctcaactag tggtgcgccg     780
gtgccgtatc cggatccgct ggaaccgcgt gccgca                                816

<210> SEQ ID NO 12
<211> LENGTH: 272
<212> TYPE: PRT
<213> ORGANISM: Artificial Sequence
<220> FEATURE:
<223> OTHER INFORMATION: scFv#E Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 12

Gln Ala Val Leu Thr Gln Pro Ser Ser Val Ser Arg Ser Leu Gly Xaa
 1               5                  10                  15

Xaa Val Ser Ile Thr Cys Ser Gly Gly Ser Ser Asn Val Gly Gln Gly
            20                  25                  30

Asp Tyr Val Ala Trp Phe Gln Gln Val Pro Gly Ser Ala Pro Lys Leu
        35                  40                  45

Leu Ile Tyr Asp Ala Thr Asn Arg Ala Ser Gly Val Pro Asp Arg Phe
    50                  55                  60

Val Gly Ser Arg Tyr Gly Asn Ser Ala Thr Leu Ile Ile Thr Ser Val
65                  70                  75                  80

Gln Ala Glu Asp Glu Ala Asp Tyr Tyr Cys Ala Ser Tyr Asp Ser Ser
                85                  90                  95

Met Tyr Thr Ile Phe Gly Ser Gly Thr Ser Leu Thr Val Leu Gly Gln
            100                 105                 110

Pro Ala Ala Ala Gly Gly Gly Gly Ser Gly Gly Gly Gly Ser Gly Gly
        115                 120                 125

Gly Gly Ser Ala Arg Gln Val Glu Leu Gln Gly Ser Gly Pro Ser Gln
    130                 135                 140

Val Lys Pro Ser Gln Thr Leu Ser Leu Ile Cys Thr Ile Ser Gly Phe
```

|       |     |     |     |     |     |     |     |     |     |     |     |     |     |     |
|-------|-----|-----|-----|-----|-----|-----|-----|-----|-----|-----|-----|-----|-----|-----|
| 145   |     |     |     | 150 |     |     |     | 155 |     |     |     | 160 |     |     |
| Ser   | Leu | Thr | Ser | Asn | Asn | Val | Ala | Trp | Val | Arg | Gln | Ala | Pro | Gly | Lys |

Ser Leu Thr Ser Asn Asn Val Ala Trp Val Arg Gln Ala Pro Gly Lys
                                        165                         170                         175

Gly Leu Glu Trp Val Gly Val Ile Ser Asp Gly Gly Thr Pro Tyr Tyr
                    180                         185                         190

Asn Ser Ala Leu Lys Ser Arg Leu Ser Ile Thr Arg Asp Thr Ser Lys
                    195                         200                         205

Ser Gln Val Ser Leu Ser Leu Ser Ser Val Thr Thr Glu Asp Thr Ala
                    210                         215                         220

Val Tyr Tyr Cys Ala Arg Thr Leu Asp Tyr Ser His Ile Trp Leu Tyr
225                         230                         235                         240

Ser Ala Asp Gln Trp Gly Pro Gly Leu Leu Val Thr Val Ser Ser Thr
                    245                         250                         255

Ser Gly Ala Pro Val Pro Tyr Pro Asp Pro Leu Glu Pro Arg Ala Ala
                    260                         265                         270

<210> SEQ ID NO 13
<211> LENGTH: 861
<212> TYPE: DNA
<213> ORGANISM: Artificial Sequence
<220> FEATURE:
<223> OTHER INFORMATION: scFv#7-2E Single Chain Antibody

<400> SEQUENCE: 13

```
ggtgcgccgg tgccgtatcc ggatccgctc gagccgcgtg ccggctccta tgaactgacc      60
cagccgcctt caatgtcggt ggccttggga cagacggcca aggtcacctg ccagggagac     120
aacttagaaa acttttatgt tcagtggcac agcagaagc cgggccaggc ccctgtgacg     180
gtcattttc aggataataa gaggccctcg gggatccctg accggttctc tggctccaac     240
tcggggaaca cggccaccct gaccatcagc ggggcccgga ccgaggacga ggccgactat     300
tactgtcagt caggccacag cagtatcggt ggtgttttcg gcagcgggac cagcctgacc     360
gtcctgggtc agcccgcggc cgctggtgga ggcggttcag gcggaggtgg ctctggcggt     420
ggcggatcgg cgcgccaggt gcagctgcag gagtcgggac ccagcctggt gaagccctca     480
cagaccctct ccctcacctg cacggtctct ggcttctcat taacgggaaa ttctgtaacc     540
tgggtccgcc aggctccagg aaacgtgccg gagtggcttg gtggtataag ccgcggtgga     600
cgcacatact atgatacggc cctgaagtcc cggctcagca tcaccaggga cacctccaag     660
aggcaagtct ccctatcact gagcagcgtg acgactgagg acacggccat gtacttctgt     720
gcaagatcgg catatagtac tctttatgat tatgagtatg ccgctgatat ctacgactgg     780
ggcccaggac tcctggtcac cgtctcctca actagtggtg cgccggtgcc gtatccggat     840
ccgctggaac gcgtgccgc a                                                 861
```

<210> SEQ ID NO 14
<211> LENGTH: 287
<212> TYPE: PRT
<213> ORGANISM: Artificial Sequence
<220> FEATURE:
<223> OTHER INFORMATION: scFv#7-2E Single Chain Antibody

<400> SEQUENCE: 14

Gly Ala Pro Val Pro Tyr Pro Asp Pro Leu Glu Pro Arg Ala Gly Ser
1                   5                       10                      15

Tyr Glu Leu Thr Gln Pro Pro Ser Met Ser Val Ala Leu Gly Gln Thr
                    20                      25                      30

Ala Lys Val Thr Cys Gln Gly Asp Asn Leu Glu Asn Phe Tyr Val Gln

```
                    35                  40                  45
Trp His Gln Gln Lys Pro Gly Gln Ala Pro Val Thr Val Ile Phe Gln
    50                  55                  60

Asp Asn Lys Arg Pro Ser Gly Ile Pro Asp Arg Phe Ser Gly Ser Asn
65                  70                  75                  80

Ser Gly Asn Thr Ala Thr Leu Thr Ile Ser Gly Ala Arg Thr Glu Asp
                85                  90                  95

Glu Ala Asp Tyr Tyr Cys Gln Ser Gly His Ser Ser Ile Gly Gly Val
            100                 105                 110

Phe Gly Ser Gly Thr Ser Leu Thr Val Leu Gly Gln Pro Ala Ala Ala
        115                 120                 125

Gly Gly Gly Gly Ser Gly Gly Gly Ser Gly Gly Gly Ser Ala
    130                 135                 140

Arg Gln Val Gln Leu Gln Glu Ser Gly Pro Ser Leu Val Lys Pro Ser
145                 150                 155                 160

Gln Thr Leu Ser Leu Thr Cys Thr Val Ser Gly Phe Ser Leu Thr Gly
                165                 170                 175

Asn Ser Val Thr Trp Val Arg Gln Ala Pro Gly Asn Val Pro Glu Trp
            180                 185                 190

Leu Gly Gly Ile Ser Arg Gly Gly Arg Thr Tyr Tyr Asp Thr Ala Leu
        195                 200                 205

Lys Ser Arg Leu Ser Ile Thr Arg Asp Thr Ser Lys Arg Gln Val Ser
    210                 215                 220

Leu Ser Leu Ser Ser Val Thr Thr Glu Asp Thr Ala Met Tyr Phe Cys
225                 230                 235                 240

Ala Arg Ser Ala Tyr Ser Thr Leu Tyr Asp Tyr Glu Tyr Ala Ala Asp
                245                 250                 255

Ile Tyr Asp Trp Gly Pro Gly Leu Leu Val Thr Val Ser Ser Thr Ser
            260                 265                 270

Gly Ala Pro Val Pro Tyr Pro Asp Pro Leu Glu Pro Arg Ala Ala
        275                 280                 285

<210> SEQ ID NO 15
<211> LENGTH: 13
<212> TYPE: PRT
<213> ORGANISM: Artificial Sequence
<220> FEATURE:
<223> OTHER INFORMATION: Epitope Tag

<400> SEQUENCE: 15

Gly Ala Pro Val Pro Tyr Pro Asp Pro Leu Glu Pro Arg
1               5                   10

<210> SEQ ID NO 16
<211> LENGTH: 9
<212> TYPE: PRT
<213> ORGANISM: Artificial Sequence
<220> FEATURE:
<223> OTHER INFORMATION: VHH binding agents

<400> SEQUENCE: 16

Gln Val Gln Leu Val Glu Ser Gly Gly
1               5

<210> SEQ ID NO 17
<211> LENGTH: 8
<212> TYPE: PRT
<213> ORGANISM: Artificial Sequence
<220> FEATURE:
<223> OTHER INFORMATION: VHH binding agents
```

-continued

<400> SEQUENCE: 17

Ala His His Ser Glu Asp Pro Ser
1               5

<210> SEQ ID NO 18
<211> LENGTH: 8
<212> TYPE: PRT
<213> ORGANISM: Artificial Sequence
<220> FEATURE:
<223> OTHER INFORMATION: VHH binding agents

<400> SEQUENCE: 18

Glu Pro Lys Thr Pro Lys Pro Gln
1               5

<210> SEQ ID NO 19
<211> LENGTH: 396
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 19

```
caggtgcagc tcgtggagtc aggaggaggc ttggtgcagc ctgggggatc tctgagactc      60
tcgtgtgtag tctctggaag tgacttcaat acctatatca tgggctggta ccgccaggtt     120
ccagggaagc cgcgcgagtt ggtcgcagat attactactg aaggaaaaac aaactatggc     180
ggctccgtaa aggacgatt caccatctcc agagacaacg ccaaaaacac ggtgtatctg     240
caaatgttcg gcctgaaacc tgaggacgcg ggtaattatg tctgtaacgc agactggaag     300
atgggtgcat ggaccgcggg ggactacggt atcgactact ggggcaaagg gaccctggtc     360
accgtctcct cagaacccaa gacaccaaaa ccacaa                              396
```

<210> SEQ ID NO 20
<211> LENGTH: 132
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Val Val Ser Gly Ser Asp Phe Asn Thr Tyr
            20                  25                  30

Ile Met Gly Trp Tyr Arg Gln Val Pro Gly Lys Pro Arg Glu Leu Val
        35                  40                  45

Ala Asp Ile Thr Thr Glu Gly Lys Thr Asn Tyr Gly Gly Ser Val Lys
    50                  55                  60

Gly Arg Phe Thr Ile Ser Arg Asp Asn Ala Lys Asn Thr Val Tyr Leu
65                  70                  75                  80

Gln Met Phe Gly Leu Lys Pro Glu Asp Ala Gly Asn Tyr Val Cys Asn
                85                  90                  95

Ala Asp Trp Lys Met Gly Ala Trp Thr Ala Gly Asp Tyr Gly Ile Asp
            100                 105                 110

Tyr Trp Gly Lys Gly Thr Leu Val Thr Val Ser Ser Glu Pro Lys Thr
        115                 120                 125

Pro Lys Pro Gln
    130

<210> SEQ ID NO 21
<211> LENGTH: 408
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 21

```
caggtgcagc tcgtggagtc cggtggaggc ttggtgcagc ctgggggtc tctgagactc      60
tcctgtgcag cctctgcagg caatctggat tattatgcca taggctggtt ccgccaggcc    120
ccagggaagg agcgcgaggg ggtctcatgt attagtagta gtgatggtag cactgtctat    180
acagactccg tgaagggccg attcaccatc tccagagaca taccaagaa cacggtagat     240
ctgcaaatgg acaatttgaa acctgaggac acggccgttt attactgtgc gacagtcgtt    300
aactactact gcacagccgg tgggtccatt cacgcgagcc cgtatgaaat ctggggccag    360
gggacccagg tcaccgtctc ctcagcgcac cacagcgaag acccctcg                408
```

<210> SEQ ID NO 22
<211> LENGTH: 136
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 22

```
Gln Val Gln Leu Val Glu Ser Gly Gly Gly Leu Val Gln Pro Gly Gly
1               5                   10                  15
Ser Leu Arg Leu Ser Cys Ala Ala Ser Ala Gly Asn Leu Asp Tyr Tyr
            20                  25                  30
Ala Ile Gly Trp Phe Arg Gln Ala Pro Gly Lys Glu Arg Glu Gly Val
        35                  40                  45
Ser Cys Ile Ser Ser Ser Asp Gly Ser Thr Val Tyr Thr Asp Ser Val
    50                  55                  60
Lys Gly Arg Phe Thr Ile Ser Arg Asp Asn Thr Lys Asn Thr Val Asp
65                  70                  75                  80
Leu Gln Met Asp Asn Leu Lys Pro Glu Asp Thr Ala Val Tyr Tyr Cys
                85                  90                  95
Ala Thr Val Val Asn Tyr Tyr Cys Thr Ala Gly Gly Ser Ile His Ala
            100                 105                 110
Ser Pro Tyr Glu Ile Trp Gly Gln Gly Thr Gln Val Thr Val Ser Ser
        115                 120                 125
Ala His His Ser Glu Asp Pro Ser
    130                 135
```

<210> SEQ ID NO 23
<211> LENGTH: 375
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 23

```
caggtgcagc tcgtggagtc cggcggaggc ttggtgcacc ctgggggtc tctgagactc      60
tcttgtgcac cctctgccag tctaccatca acacccttca accccttcaa caatatggtg    120
ggctggtacc gtcaggctcc aggtaaacag cgcgaaatgg tcgcaagtat tggtctacga    180
ataaactatg cagactccgt gaagggccga ttcaccatct ccagagacaa cgccaagaac    240
acggtggatc tgcagatgga cagcctgcga cctgaggact cagccacata ctactgtcat    300
```

```
atagaataca cccactactg gggcaaaggg accctggtca ccgtctcctc ggaacccaag    360
acaccaaaac cacaa                                                    375

<210> SEQ ID NO 24
<211> LENGTH: 133
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 24

Gln Val Gln Leu Val Glu Ser Gly Gly Gly Leu Val His Pro Gly Gly
1               5                   10                  15

Ser Leu Arg Leu Ser Cys Ala Pro Ser Ala Ser Leu Pro Ser Thr Pro
            20                  25                  30

Phe Asn Pro Phe Asn Asn Met Val Gly Trp Tyr Arg Gln Ala Pro Gly
        35                  40                  45

Lys Gln Arg Glu Met Val Ala Ser Ile Gly Leu Arg Ile Asn Tyr Ala
    50                  55                  60

Asp Ser Val Lys Gly Arg Phe Thr Ile Ser Arg Asp Asn Ala Lys Asn
65                  70                  75                  80

Thr Val Asp Leu Gln Met Asp Ser Leu Arg Pro Glu Asp Ser Ala Thr
                85                  90                  95

Tyr Tyr Cys His Ile Glu Tyr Thr His Tyr Trp Gly Lys Gly Thr Leu
            100                 105                 110

Val Thr Val Ser Ser Glu Pro Lys Thr Pro Lys Pro Gln Glu Pro Lys
        115                 120                 125

Thr Pro Lys Pro Gln
    130

<210> SEQ ID NO 25
<211> LENGTH: 378
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 25
caggtgcagc tcgtggagtc tgtggaggc ttggcgcagc ctggggggtc tctgagactc    60
tcctgtgaag cgtctggttt tgggacatgg ttcaggttcg atgagaacac cgtgaactgg    120
taccgccagc tccaggaaa gtcgcgcgag ttcgacgagt tggtcgctcg ttacccaaaa    180
agtggcatcg taacctattt agactccgtg aagggccgat tcacgatctc cagagacaac    240
gccaaaaaaa tggcgtttct gcaaatggac aacctgaaac tgaggacac ggccgtctat    300 tattgcaatg tcggtgaatt tgggggccag gggacccagg tcacgatctc ctcagaaccc    360
aagacaccaa aaccacaa                                                 378

<210> SEQ ID NO 26
<211> LENGTH: 126
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 26

Gln Val Gln Leu Val Glu Ser Gly Gly Gly Leu Ala Gln Pro Gly Gly
1               5                   10                  15

Ser Leu Arg Leu Ser Cys Glu Ala Ser Gly Phe Gly Thr Trp Phe Arg
```

```
                20                  25                  30
Phe Asp Glu Asn Thr Val Asn Trp Tyr Arg Gln Pro Pro Gly Lys Ser
        35                  40                  45

Arg Glu Phe Asp Glu Leu Val Ala Arg Tyr Pro Lys Ser Gly Ile Val
    50                  55                  60

Thr Tyr Leu Asp Ser Val Lys Gly Arg Phe Thr Ile Ser Arg Asp Asn
65                  70                  75                  80

Ala Lys Lys Met Ala Phe Leu Gln Met Asp Asn Leu Lys Pro Glu Asp
                85                  90                  95

Thr Ala Val Tyr Tyr Cys Asn Val Gly Glu Phe Trp Gly Gln Gly Thr
            100                 105                 110

Gln Val Thr Ile Ser Ser Glu Pro Lys Thr Pro Lys Pro Gln
        115                 120                 125

<210> SEQ ID NO 27
<211> LENGTH: 384
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 27
caggtgcagc tcgtggagtc ggggggaggc ttggtgcagc ctgggggggtc tctgagactc     60 tcctgtgcag cctctggatt caccctaggg tcgcgttaca tgagctgggt ccgccaggct    120
ccaggagagg ggttcgagtg gtctcaagt attgaaccct ctggtaccgc atgggatgga    180
gactccgcga agggacgatt caccacttcc agagacgacg ccaagaacac gctttatctg    240
caaatgagca acctgcaacc cgaggacacg ggtgtttatt actgtgcaac agggtatcgg    300
acggacacga ggattccggg tggctcgtgg ggccagggga cccaggtcac cgtctcctca    360
gaacccaaga caccaaaacc acaa                                          384

<210> SEQ ID NO 28
<211> LENGTH: 128
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 28

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Gly Ser Arg
            20                  25                  30

Tyr Met Ser Trp Val Arg Gln Ala Pro Gly Glu Gly Phe Glu Trp Val
        35                  40                  45

Ser Ser Ile Glu Pro Ser Gly Thr Ala Trp Asp Gly Asp Ser Ala Lys
    50                  55                  60

Gly Arg Phe Thr Thr Ser Arg Asp Asp Ala Lys Asn Thr Leu Tyr Leu
65                  70                  75                  80

Gln Met Ser Asn Leu Gln Pro Glu Asp Thr Gly Val Tyr Tyr Cys Ala
                85                  90                  95

Thr Gly Tyr Arg Thr Asp Thr Arg Ile Pro Gly Gly Ser Trp Gly Gln
            100                 105                 110

Gly Thr Gln Val Thr Val Ser Ser Glu Pro Lys Thr Pro Lys Pro Gln
        115                 120                 125

<210> SEQ ID NO 29
```

```
<211> LENGTH: 360
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 29
caggtgcagc tcgtggagtc tggaggaggc ttggtgcagc ctggggggtc tctgagactc        60
tcctgtcaag tctctggatt caccttcggt gactgggtca tgagctggtt ccgccaggct       120
ccggggaagg agcgcgaatt cgtcgcaagt attacggcta ctagtagtct aaagtattat       180
gcagactccg tgaagggccg attcaccatc tccagagaca atgtcaacaa cacactgttt       240
ctgcaaatgg atcgcctgaa atctgaggac acggccgttt attactgtcg gtcccccaac       300
tactggggcc agggacccca ggtcaccgtc tccgccgaac ccaagacacc aaaaccacaa       360

<210> SEQ ID NO 30
<211> LENGTH: 120
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Gln Val Ser Gly Phe Thr Phe Gly Asp Trp
            20                  25                  30

Val Met Ser Trp Phe Arg Gln Ala Pro Gly Lys Glu Arg Glu Phe Val
        35                  40                  45

Ala Ser Ile Thr Ala Thr Ser Ser Leu Lys Tyr Tyr Ala Asp Ser Val
    50                  55                  60

Lys Gly Arg Phe Thr Ile Ser Arg Asp Asn Val Asn Asn Thr Leu Phe
65                  70                  75                  80

Leu Gln Met Asp Arg Leu Lys Ser Glu Asp Thr Ala Val Tyr Tyr Cys
                85                  90                  95

Arg Ser Pro Asn Tyr Trp Gly Gln Gly Thr Gln Val Thr Val Ser Ala
            100                 105                 110

Glu Pro Lys Thr Pro Lys Pro Gln
        115                 120

<210> SEQ ID NO 31
<211> LENGTH: 366
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 31
caggtgcagc tcgtggagtc aggtggaggc ttggtgcagg ttgggggggtc tctgagactc        60 tcctgtgtag tttctggaag cgacatcagt ggcattgcga tgggctggta ccgccaggct       120
ccagggaagc ggcgcgaaat ggtcgcagat atttttctg gcggtagtac agactatgca       180
ggctccgtga agggccgatt caccatctcc agagacaacg ccaagaagac gagctatctg       240
caaatgaaca acgtgaaacc tgaggacacc ggagtctact actgtaggct gtacgggagc       300
ggtgactact ggggccaggg gacccaggtc accgtctcct cagcgcacca cagcgaagac       360
ccctcg                                                                   366

<210> SEQ ID NO 32
```

```
<211> LENGTH: 122
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 32

Gln Val Gln Leu Val Glu Ser Gly Gly Gly Leu Val Gln Val Gly Gly
1               5                   10                  15

Ser Leu Arg Leu Ser Cys Val Val Ser Gly Ser Asp Ile Ser Gly Ile
            20                  25                  30

Ala Met Gly Trp Tyr Arg Gln Ala Pro Gly Lys Arg Arg Glu Met Val
        35                  40                  45

Ala Asp Ile Phe Ser Gly Gly Ser Thr Asp Tyr Ala Gly Ser Val Lys
    50                  55                  60

Gly Arg Phe Thr Ile Ser Arg Asp Asn Ala Lys Lys Thr Ser Tyr Leu
65                  70                  75                  80

Gln Met Asn Asn Val Lys Pro Glu Asp Thr Gly Val Tyr Tyr Cys Arg
                85                  90                  95

Leu Tyr Gly Ser Gly Asp Tyr Trp Gly Gln Gly Thr Gln Val Thr Val
            100                 105                 110

Ser Ser Ala His His Ser Glu Asp Pro Ser
        115                 120

<210> SEQ ID NO 33
<211> LENGTH: 411
<212> TYPE: DNA
<213> ORGANISM: Artificial Sequence
<220> FEATURE:
<223> OTHER INFORMATION: VHH binding agents specific to BoNT/B holotoxin

<400> SEQUENCE: 33
caggtgcagc tcgtggagtc aggcggaggc ttggtgcagc ctggggggtc tctgaaactc        60
tcctgtgcag cctctggatt cactttggga caccatcgcg ttggctggtt ccgccaggcc       120
ccaggaaaga agcgtgaggg ggtcgcgtgt attagcgcca ctggtcttag cacacactat       180
tcagactccg tgaccggccg atttaccgtc tccagagaca acctcaacaa cgtggcgtat       240
ctgcagctga acagcctgaa acctgaggac gcaggtgttt attactgtgc aagcagattc       300
tcccttaatt cggtcgatgc gaatatgtgc ctttcagagc tcagtatgca caactggggc       360
caggggaccc aggtcagaat ctcctcagaa cccaagacac caaaaccaca a                411

<210> SEQ ID NO 34
<211> LENGTH: 137
<212> TYPE: PRT
<213> ORGANISM: Artificial Sequence
<220> FEATURE:
<223> OTHER INFORMATION: VHH binding agents specific to BoNT/B holotoxin

<400> SEQUENCE: 34

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Leu Gly His His
            20                  25                  30

Arg Val Gly Trp Phe Arg Gln Ala Pro Gly Lys Lys Arg Glu Gly Val
        35                  40                  45

Ala Cys Ile Ser Ala Thr Gly Leu Ser Thr His Tyr Ser Asp Ser Val
    50                  55                  60

Thr Gly Arg Phe Thr Val Ser Arg Asp Asn Leu Asn Asn Val Ala Tyr
65                  70                  75                  80
```

```
Leu Gln Leu Asn Ser Leu Lys Pro Glu Asp Ala Gly Val Tyr Tyr Cys
                85                  90                  95

Ala Ser Arg Phe Ser Leu Asn Ser Val Asp Ala Asn Met Cys Leu Ser
            100                 105                 110

Glu Pro Gln Tyr Asp Asn Trp Gly Gln Gly Thr Gln Val Arg Ile Ser
        115                 120                 125

Ser Glu Pro Lys Thr Pro Lys Pro Gln
    130                 135
```

<210> SEQ ID NO 35
<211> LENGTH: 399
<212> TYPE: DNA
<213> ORGANISM: Artificial Sequence
<220> FEATURE:
<223> OTHER INFORMATION: VHH binding agents specific to BoNT/B holotoxin

<400> SEQUENCE: 35

```
caggtgcagc tcgtggagac gggtggagga ttggtgcagg ccggggggctc tctgagactc     60 tcctgcgcag gctctggacg ctccttcagc gccgctgtca tgggctggtt ccgccaggcg    120
ccagggaagg agcgagaatt cgtagcagca cttagacaaa ttattggtag cacacactat    180
gcagactccg tgaagggccg attcaccatc tccagagaca cgccaagaa catgttgtat    240 ctcgacatga acagcctgaa acctacggac acggccgcgt attactgcac agcgggacct    300
ccgactatgc tggacgtttc taccgaccgg gagtatgaca cctggggtca ggggactcag    360
gtcaccgtct cctcagcgca ccacagcgaa gaccctcg                            399
```

<210> SEQ ID NO 36
<211> LENGTH: 133
<212> TYPE: PRT
<213> ORGANISM: Artificial Sequence
<220> FEATURE:
<223> OTHER INFORMATION: VHH binding agents specific to BoNT/B holotoxin

<400> SEQUENCE: 36

```
Gln Val Gln Leu Val Glu Ser Gly Gly Gly Leu Val Gln Ala Gly Gly
1               5                   10                  15

Ser Leu Arg Leu Ser Cys Ala Gly Ser Gly Arg Ser Phe Ser Ala Ala
            20                  25                  30

Val Met Gly Trp Phe Arg Gln Ala Pro Gly Lys Glu Arg Glu Phe Val
        35                  40                  45

Ala Ala Leu Arg Gln Ile Ile Gly Ser Thr His Tyr Ala Asp Ser Val
    50                  55                  60

Lys Gly Arg Phe Thr Ile Ser Arg Asp Asn Ala Lys Asn Met Leu Tyr
65                  70                  75                  80

Leu Asp Met Asn Ser Leu Lys Pro Thr Asp Thr Ala Ala Tyr Tyr Cys
                85                  90                  95

Thr Ala Gly Pro Pro Thr Met Leu Asp Val Ser Thr Asp Arg Glu Tyr
            100                 105                 110

Asp Thr Trp Gly Gln Gly Thr Gln Val Thr Val Ser Ser Ala His His
        115                 120                 125

Ser Glu Asp Pro Ser
    130
```

<210> SEQ ID NO 37
<211> LENGTH: 363
<212> TYPE: DNA
<213> ORGANISM: Artificial Sequence
<220> FEATURE:

<223> OTHER INFORMATION: VHH binding agent

<400> SEQUENCE: 37

```
caggtgcagc tcgtggagtc cggaggaggc ttggtgcgac ctgggggtc tctgagactc      60
tcttgtgtag tctctggatt cgcctacgaa atgcccatga tgggctggta ccgccaggct    120
ccagggaatc agcgcgagtt ggtcgcaact attggtacag gtggtaggat gaactatgca    180
gactccgtga aggccgatt caccatctcc agagacaacg ccaagaacac ggtgtatctg    240
caaatgaaca gcctgaaacc tgaggacaca gccgcctatt actgtaaaat cgagtttaca    300
aattactggg gccaggggac ccaagtcacc gtctcctcag aacccaagac accaaaacca    360
caa                                                                  363
```

<210> SEQ ID NO 38
<211> LENGTH: 121
<212> TYPE: PRT
<213> ORGANISM: Artificial Sequence
<220> FEATURE:
<223> OTHER INFORMATION: VHH binding agent

<400> SEQUENCE: 38

Gln Val Gln Leu Val Glu Ser Gly Gly Gly Leu Val Arg Pro Gly Gly
1               5                   10                  15
Ser Leu Arg Leu Ser Cys Val Val Ser Gly Phe Ala Tyr Glu Met Pro
            20                  25                  30
Met Met Gly Trp Tyr Arg Gln Ala Pro Gly Asn Gln Arg Glu Leu Val
        35                  40                  45
Ala Thr Ile Gly Thr Gly Gly Arg Met Asn Tyr Ala Asp Ser Val Lys
    50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Ala Ala Tyr Tyr Cys Lys
                85                  90                  95
Ile Glu Phe Thr Asn Tyr Trp Gly Gln Gly Thr Gln Val Thr Val Ser
            100                 105                 110
Ser Glu Pro Lys Thr Pro Lys Pro Gln
        115                 120

<210> SEQ ID NO 39
<211> LENGTH: 366
<212> TYPE: DNA
<213> ORGANISM: Artificial Sequence
<220> FEATURE:
<223> OTHER INFORMATION: VHH binding agent

<400> SEQUENCE: 39

```
caggtgcagc tcgtggagtc aggtggaggc ttggtgcagc cggggggatc tctgagactg      60
tcctgtacag tctctggaag catcttcgat ctacctggaa tgaactggta tcgccaggct    120
ccagggcgc agcgcgagtt ggtcgcagat attagtagtg atggtaggag acaaactat      180
gcagactccg tgaagggccg attcaccatg tccagagaca tgccaagaa acggtgtat     240
ctgcaaatgg acagcctgaa acctgacgac acggccgtct attactgtaa tgtgaaattt    300
actcaccact ggggccaggg gatccaggtc accgtctcct cagaacccaa gacaccaaaa    360
ccacaa                                                               366
```

<210> SEQ ID NO 40
<211> LENGTH: 122
<212> TYPE: PRT

```
<213> ORGANISM: Artificial Sequence
<220> FEATURE:
<223> OTHER INFORMATION: VHH binding agent

<400> SEQUENCE: 40

Gln Val Gln Leu Val Glu Ser Gly Gly Gly Leu Val Gln Pro Gly Gly
1               5                   10                  15

Ser Leu Arg Leu Ser Cys Thr Val Ser Gly Ser Ile Phe Asp Leu Pro
            20                  25                  30

Gly Met Asn Trp Tyr Arg Gln Ala Pro Gly Ala Gln Arg Glu Leu Val
        35                  40                  45

Ala Asp Ile Ser Ser Asp Gly Arg Arg Thr Asn Tyr Ala Asp Ser Val
    50                  55                  60

Lys Gly Arg Phe Thr Met Ser Arg Asp Asn Ala Lys Lys Thr Val Tyr
65                  70                  75                  80

Leu Gln Met Asp Ser Leu Lys Pro Asp Asp Thr Ala Val Tyr Tyr Cys
                85                  90                  95

Asn Val Lys Phe Thr His His Trp Gly Gly Ile Gln Val Thr Val
            100                 105                 110

Ser Ser Glu Pro Lys Thr Pro Lys Pro Gln
        115                 120

<210> SEQ ID NO 41
<211> LENGTH: 366
<212> TYPE: DNA
<213> ORGANISM: Artificial Sequence
<220> FEATURE:
<223> OTHER INFORMATION: VHH binding agent

<400> SEQUENCE: 41
caggtgcagc tcgtggagtc aggcggaggc ttggtgcagc cggggggatc tctgaggctg      60
tcctgtacgg tctctggaag catcttcggc tacctggca tgagctggta tcgccaggct     120 ccagggcgc agcgcgagtt ggtcgcagat attagtagtg atggtgggag gacgcactat     180
gcagactccg tgaagggccg cttcaccatc tccagagaca tgacaagaa aacggtgtat     240 ctgcagatgg acagcctgaa acctgacgac acggccgtct attactgtaa tgtgaaattt     300
actcaccact ggggccaggg gatccaggtc accgtctcct cagaacccaa gacaccaaaa     360
ccacaa                                                                366

<210> SEQ ID NO 42
<211> LENGTH: 122
<212> TYPE: PRT
<213> ORGANISM: Artificial Sequence
<220> FEATURE:
<223> OTHER INFORMATION: VHH binding agent

<400> SEQUENCE: 42

Gln Val Gln Leu Val Glu Ser Gly Gly Gly Leu Val Gln Pro Gly Gly
1               5                   10                  15

Ser Leu Arg Leu Ser Cys Thr Val Ser Gly Ser Ile Phe Gly Leu Pro
            20                  25                  30

Gly Met Ser Trp Tyr Arg Gln Ala Pro Gly Ala Gln Arg Glu Leu Val
        35                  40                  45

Ala Asp Ile Ser Ser Asp Gly Gly Arg Thr His Tyr Ala Asp Ser Val
    50                  55                  60

Lys Gly Arg Phe Thr Ile Ser Arg Asp Asn Asp Lys Lys Thr Val Tyr
65                  70                  75                  80

Leu Gln Met Asp Ser Leu Lys Pro Asp Asp Thr Ala Val Tyr Tyr Cys
```

```
                       85                  90                  95
Asn Val Lys Phe Thr His His Trp Gly Gln Gly Ile Gln Val Thr Val
                100                 105                 110
Ser Ser Glu Pro Lys Thr Pro Lys Pro Gln
        115                 120

<210> SEQ ID NO 43
<211> LENGTH: 366
<212> TYPE: DNA
<213> ORGANISM: Artificial Sequence
<220> FEATURE:
<223> OTHER INFORMATION: VHH binding agent

<400> SEQUENCE: 43
caggtgcagc tcgtggagtc tgggggaggc ttggtgcagg atggggggtc tctgaggctc      60
tcctgcacaa catctggaag tatcgacagt ttcaatgcca tagagtggta ccgccaggct     120
ccagggaagc agcgcgaatt ggtcgcaagt ataagtagtg atggtcgtcg cacaaactat     180
gcagactccg tgaagggccg attcaccatc tccggagaca cgccaagaa cacggtgtat      240 ctgcaaatga acagcctgaa acctgaggac acagccgtgt attactgtca tagaccttt      300 acccactact ggggccaggg gacccaggtc accgtctcct cagaacccaa gacaccaaaa     360
ccacaa                                                                366

<210> SEQ ID NO 44
<211> LENGTH: 122
<212> TYPE: PRT
<213> ORGANISM: Artificial Sequence
<220> FEATURE:
<223> OTHER INFORMATION: VHH binding agent

<400> SEQUENCE: 44

Gln Val Gln Leu Val Glu Ser Gly Gly Gly Leu Val Gln Asp Gly Gly
1               5                   10                  15

Ser Leu Arg Leu Ser Cys Thr Thr Ser Gly Ser Ile Asp Ser Phe Asn
            20                  25                  30

Ala Ile Glu Trp Tyr Arg Gln Ala Pro Gly Lys Gln Arg Glu Leu Val
        35                  40                  45

Ala Ser Ile Ser Ser Asp Gly Arg Arg Thr Asn Tyr Ala Asp Ser Val
    50                  55                  60

Lys Gly Arg Phe Thr Ile Ser Gly Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

His Arg Pro Phe Thr His Tyr Trp Gly Gln Gly Thr Gln Val Thr Val
                100                 105                 110

Ser Ser Glu Pro Lys Thr Pro Lys Pro Gln
        115                 120

<210> SEQ ID NO 45
<211> LENGTH: 912
<212> TYPE: DNA
<213> ORGANISM: Artificial Sequence
<220> FEATURE:
<223> OTHER INFORMATION: VHH binding agent with tag

<400> SEQUENCE: 45
atgagcgata aaattattca cctgactgac gacagttttg acacggatgt actcaaagcg      60 gacgggggcga tcctcgtcga tttctgggca gagtggtgcg gtccgtgcaa aatgatcgcc    120
```

```
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg ccatatgca ccatcatcat    360 catcattctt ctggtctggt gccacgcggt tctggtatga agaaaccgc tgctgctaaa    420 ttcgaacgcc agcacatgga cagcccagat ctgggtaccg acgacgacga caaggccatg    480
gcgatatcgg atccgaattc ccaggtgcag ctcgtggagt caggtggagg cttggtgcag    540 gttgggggt ctctgagact ctcctgtgta gtttctggaa cgacatcag tggcattgcg    600 atgggctggt accgccaggc tccagggaag cggcgcgaaa tggtcgcaga tattttttct    660
ggcggtagta cagactatgc aggctccgtg aagggccgat tcaccatctc cagagacaac    720
gccaagaaga cgagctatct gcaaatgaac aacgtgaaac tgaggacac cggagtctac    780 tactgtaggc tgtacgggag cggtgactac tggggccagg ggacccaggt caccgtctcc    840
tcagcgcacc acagcgaaga ccccactagt ggtgcgccgg tgccgtatcc ggatccgctg    900
gaaccgcgtt aa                                                        912
```

```
<210> SEQ ID NO 46
<211> LENGTH: 303
<212> TYPE: PRT
<213> ORGANISM: Artificial Sequence
<220> FEATURE:
<223> OTHER INFORMATION: VHH binding agent with tag

<400> SEQUENCE: 46

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
            115                 120                 125

Arg Gly Ser Gly Met Lys Glu Thr Ala Ala Ala Lys Phe Glu Arg Gln
        130                 135                 140

His Met Asp Ser Pro Asp Leu Gly Thr Asp Asp Asp Lys Ala Met
145                 150                 155                 160

Ala Ile Ser Asp Pro Asn Ser Gln Val Gln Leu Val Glu Ser Gly Gly
                165                 170                 175

Gly Leu Val Gln Val Gly Gly Ser Leu Arg Leu Ser Cys Val Val Ser
            180                 185                 190

Gly Ser Asp Ile Ser Gly Ile Ala Met Gly Trp Tyr Arg Gln Ala Pro
        195                 200                 205

Gly Lys Arg Arg Glu Met Val Ala Asp Ile Phe Ser Gly Gly Ser Thr
    210                 215                 220
```

```
Asp Tyr Ala Gly Ser Val Lys Gly Arg Phe Thr Ile Ser Arg Asp Asn
225                 230                 235                 240

Ala Lys Lys Thr Ser Tyr Leu Gln Met Asn Asn Val Lys Pro Glu Asp
            245                 250                 255

Thr Gly Val Tyr Tyr Cys Arg Leu Tyr Gly Ser Gly Asp Tyr Trp Gly
        260                 265                 270

Gln Gly Thr Gln Val Thr Val Ser Ser Ala His His Ser Glu Asp Pro
    275                 280                 285

Thr Ser Gly Ala Pro Val Pro Tyr Pro Asp Pro Leu Glu Pro Arg
    290                 295                 300

<210> SEQ ID NO 47
<211> LENGTH: 924
<212> TYPE: DNA
<213> ORGANISM: Artificial Sequence
<220> FEATURE:
<223> OTHER INFORMATION: VHH binding agent with tag

<400> SEQUENCE: 47
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggt tctggttctg ccatatgca ccatcatcat      360 catcattctt ctggtctggt gccacgcggt tctggtatga agaaaccgc tgctgctaaa      420 ttcgaacgcc agcacatgga cagcccagat ctgggtaccg acgacgacga caaggccatg     480
gcgatatcgg atccgaattc ccaggtgcag ctcgtggagt ccggcggagg cttggtgcac     540 cctgggggt ctctgagact ctcttgtgca ccctctgcca gtctaccatc aacacccttc      600
aacccctcca caatatggt gggctggtac cgtcaggctc aggtaaaaca gcgcgaaatg      660
gtcgcaagta ttggtctacg aataaaactat gcagactccg tgaagggccg attcaccatc      720
tccagagaca acgccaagaa cacggtggat ctgcagatgg acagcctgcg acctgaggac     780
tcagccacat actactgtca tatagaatac ccccactact ggggcaaagg gaccctggtc     840
accgtctcct cggaacccaa gacaccaaaa ccacaaacta gtggtgcgcc ggtgccgtat     900
ccggatccgc tggaaccgcg ttaa                                             924

<210> SEQ ID NO 48
<211> LENGTH: 307
<212> TYPE: PRT
<213> ORGANISM: Artificial Sequence
<220> FEATURE:
<223> OTHER INFORMATION: VHH binding agent with tag

<400> SEQUENCE: 48

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
```

```
               65                  70                  75                  80
Leu Phe Lys Asn Gly Glu Val Ala Ala Thr Lys Val Gly Ala Leu Ser
                    85                  90                  95
Lys Gly Gln Leu Lys Glu Phe Leu Asp Ala Asn Leu Ala Gly Ser Gly
                    100                 105                 110
Ser Gly His Met His His His His His His Ser Ser Gly Leu Val Pro
                    115                 120                 125
Arg Gly Ser Gly Met Lys Glu Thr Ala Ala Ala Lys Phe Glu Arg Gln
        130                 135                 140
His Met Asp Ser Pro Asp Leu Gly Thr Asp Asp Asp Lys Ala Met
145                 150                 155                 160
Ala Ile Ser Asp Pro Asn Ser Gln Val Gln Leu Val Glu Ser Gly Gly
                    165                 170                 175
Gly Leu Val His Pro Gly Gly Ser Leu Arg Leu Ser Cys Ala Pro Ser
                    180                 185                 190
Ala Ser Leu Pro Ser Thr Pro Phe Asn Pro Phe Asn Asn Met Val Gly
                    195                 200                 205
Trp Tyr Arg Gln Ala Pro Gly Lys Gln Arg Glu Met Val Ala Ser Ile
        210                 215                 220
Gly Leu Arg Ile Asn Tyr Ala Asp Ser Val Lys Gly Arg Phe Thr Ile
225                 230                 235                 240
Ser Arg Asp Asn Ala Lys Asn Thr Val Asp Leu Gln Met Asp Ser Leu
                    245                 250                 255
Arg Pro Glu Asp Ser Ala Thr Tyr Tyr Cys His Ile Glu Tyr Thr His
                    260                 265                 270
Tyr Trp Gly Lys Gly Thr Leu Val Thr Val Ser Ser Glu Pro Lys Thr
        275                 280                 285
Pro Lys Pro Gln Thr Ser Gly Ala Pro Val Pro Tyr Pro Asp Pro Leu
        290                 295                 300
Glu Pro Arg
305

<210> SEQ ID NO 49
<211> LENGTH: 1350
<212> TYPE: DNA
<213> ORGANISM: Artificial Sequence
<220> FEATURE:
<223> OTHER INFORMATION: VHH dimer binding agent with tag

<400> SEQUENCE: 49
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatatgca ccatcatcat   360
catcattctt ctggtctggt gccacgcggt tctggtatga agaaaccgc tgctgctaaa   420 ttcgaacgcc agcacatgga cagcccagat ctgggtaccg acgacgacga caaggccatg   480
gcggccgctc aggtgcagct cgtggagtca ggtgaggct tggtgcaggt tgggggtct   540 ctgagactct cctgtgtagt ttctggaagc gacatcagtg gcattgcgat gggctggtac   600
cgccaggctc cagggaagcg gcgcgaaatg gtcgcagata tttttctctgg cggtagtaca   660 gactatgcag gctccgtgaa gggccgattc accatctcca gagacaacgc caagaagacg   720
```

-continued

```
agctatctgc aaatgaacaa cgtgaaacct gaggacaccg gagtctacta ctgtaggctg    780
tacgggagcg gtgactactg gggccagggg acccaggtca ccgtctcctc agcgcaccac    840
agcgaagacc ccactagtgc gatcgctggt ggaggcggtt caggcggagg tggctctggc    900
ggtggcggtt ccctgcaggg tcagttgcag ctcgtggagt ccggcggagg cttggtgcac    960
cctgggggt ctctgagact ctcttgtgca ccctctgcca gtctaccatc aacacccttc    1020
aacccctca acaatatggt gggctggtac cgtcaggctc aggtaaaca gcgcgaaatg    1080
gtcgcaagta ttggtctacg aataaactat gcagactccg tgaagggccg attcaccatc    1140
tccagagaca acgccaagaa cacggtggat ctgcagatgg acagcctgcg acctgaggac    1200
tcagccacat actactgtca tatagaatac acccactact ggggcaaagg gaccctggtc    1260
accgtctcct cggaacccaa gacaccaaaa ccacaaccgg cgcgccaggg tgcgccggtg    1320
ccgtatccgg acccgctgga accgcgttaa                                    1350
```

<210> SEQ ID NO 50
<211> LENGTH: 449
<212> TYPE: PRT
<213> ORGANISM: Artificial Sequence
<220> FEATURE:
<223> OTHER INFORMATION: VHH dimer binding agent with tag

<400> SEQUENCE: 50

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Ala Ala Ala Gln Val Gln Leu Val Glu Ser Gly Gly Gly Leu Val Gln
                165                 170                 175

Val Gly Gly Ser Leu Arg Leu Ser Cys Val Val Ser Gly Ser Asp Ile
            180                 185                 190

Ser Gly Ile Ala Met Gly Trp Tyr Arg Gln Ala Pro Gly Lys Arg Arg
        195                 200                 205

Glu Met Val Ala Asp Ile Phe Ser Gly Gly Ser Thr Asp Tyr Ala Gly
    210                 215                 220

Ser Val Lys Gly Arg Phe Thr Ile Ser Arg Asp Asn Ala Lys Lys Thr
225                 230                 235                 240

Ser Tyr Leu Gln Met Asn Asn Val Lys Pro Glu Asp Thr Gly Val Tyr
                245                 250                 255
```

-continued

Tyr Cys Arg Leu Tyr Gly Ser Gly Asp Tyr Trp Gly Gln Gly Thr Gln
            260                 265                 270

Val Thr Val Ser Ser Ala His His Ser Glu Asp Pro Thr Ser Ala Ile
        275                 280                 285

Ala Gly Gly Gly Ser Gly Gly Gly Ser Gly Gly Gly Ser
    290                 295                 300

Leu Gln Gly Gln Leu Gln Leu Val Glu Ser Gly Gly Leu Val His
305                 310                 315                 320

Pro Gly Gly Ser Leu Arg Leu Ser Cys Ala Pro Ser Ala Ser Leu Pro
                325                 330                 335

Ser Thr Pro Phe Asn Pro Phe Asn Asn Met Val Gly Trp Tyr Arg Gln
                340                 345                 350

Ala Pro Gly Lys Gln Arg Glu Met Val Ala Ser Ile Gly Leu Arg Ile
                355                 360                 365

Asn Tyr Ala Asp Ser Val Lys Gly Arg Phe Thr Ile Ser Arg Asp Asn
370                 375                 380

Ala Lys Asn Thr Val Asp Leu Gln Met Asp Ser Leu Arg Pro Glu Asp
385                 390                 395                 400

Ser Ala Thr Tyr Tyr Cys His Ile Glu Tyr Thr His Tyr Trp Gly Lys
                405                 410                 415

Gly Thr Leu Val Thr Val Ser Ser Glu Pro Lys Thr Pro Lys Pro Gln
            420                 425                 430

Pro Ala Arg Gln Gly Ala Pro Val Pro Tyr Pro Asp Pro Leu Glu Pro
            435                 440                 445

Arg

<210> SEQ ID NO 51
<211> LENGTH: 1410
<212> TYPE: DNA
<213> ORGANISM: Artificial Sequence
<220> FEATURE:
<223> OTHER INFORMATION: VHH dimer binding agent with two tags

<400> SEQUENCE: 51
atgagcgata aaattattca cctgactgac gacagttttg acacggatgt actcaaagcg    60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg ccatatgca ccatcatcat    360 catcattctt ctggtctggt gccacgcggt tctggtatga agaaaccgc tgctgctaaa    420 ttcgaacgcc agcacatgga cagcccagat ctgggtaccg acgacgacga caaggccatg    480
gcgatatcgg atccgaattc tggcgcacct gtcccatacc cagaccctct ggaaccacga    540
gcggccgctc aggtgcagct cgtggagtca ggtggaggct tggtgcaggt tggggggtct    600
ctgagactct cctgtgtagt ttctggaagc gacatcagtg gcattgcgat gggctggtac    660
cgccaggctc cagggaagcg cgcgaaatg gtcgcagata tttttctgg cggtagtaca    720 gactatgcag gctccgtgaa gggccgattc accatctcca gagacaacgc caagaagacg    780
agctatctgc aaatgaacaa cgtgaaacct gaggacaccg cagtctacta ctgtaggctg    840
tacgggagcg gtgactactg gggccagggg acccaggtca ccgtctcctc agcgcaccac    900
agcgaagacc ccactagtgc gatcgctggt ggaggcggtt caggcggagg tggctctggc    960

```
ggtggcggtt ccctgcaggg tcagttgcag ctcgtggagt ccggcggagg cttggtgcac    1020 cctgggggt ctctgagact ctcttgtgca ccctctgcca gtctaccatc aacacccttc     1080
aaccccttca acaatatggt gggctggtac cgtcaggctc caggtaaaca gcgcgaaatg    1140
gtcgcaagta ttggtctacg aataaactat gcagactccg tgaagggccg attcaccatc   1200
tccagagaca cgccaagaa cacggtggat ctgcagatgg acagcctgcg acctgaggac    1260
tcagccacat actactgtca tatagaatac acccactact ggggcaaagg gaccctggtc   1320
accgtctcct cggaacccaa gacaccaaaa ccacaaccgg cgcgccaggg tgcgccggtg   1380
ccgtatccgg acccgctgga accgcgttaa                                    1410
```

<210> SEQ ID NO 52
<211> LENGTH: 469
<212> TYPE: PRT
<213> ORGANISM: Artificial Sequence
<220> FEATURE:
<223> OTHER INFORMATION: VHH dimer binding agent with two tags

<400> SEQUENCE: 52

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Ala Ile Ser Asp Pro Asn Ser Gly Ala Pro Val Pro Tyr Pro Asp Pro
                165                 170                 175

Leu Glu Pro Arg Ala Ala Ala Gln Val Gln Leu Val Glu Ser Gly Gly
            180                 185                 190

Gly Leu Val Gln Val Gly Gly Ser Leu Arg Leu Ser Cys Val Val Ser
        195                 200                 205

Gly Ser Asp Ile Ser Gly Ile Ala Met Gly Trp Tyr Arg Gln Ala Pro
    210                 215                 220

Gly Lys Arg Arg Glu Met Val Ala Asp Ile Phe Ser Gly Gly Ser Thr
225                 230                 235                 240

Asp Tyr Ala Gly Ser Val Lys Gly Arg Phe Thr Ile Ser Arg Asp Asn
                245                 250                 255

Ala Lys Lys Thr Ser Tyr Leu Gln Met Asn Asn Val Lys Pro Glu Asp
            260                 265                 270

Thr Gly Val Tyr Tyr Cys Arg Leu Tyr Gly Ser Gly Asp Tyr Trp Gly
        275                 280                 285
```

Gln Gly Thr Gln Val Thr Val Ser Ser Ala His His Ser Glu Asp Pro
    290                 295                 300

Thr Ser Ala Ile Ala Gly Gly Gly Ser Gly Gly Gly Ser Gly
305                 310                 315                 320

Gly Gly Gly Ser Leu Gln Gly Gln Leu Gln Leu Val Glu Ser Gly Gly
                325                 330                 335

Gly Leu Val His Pro Gly Gly Ser Leu Arg Leu Ser Cys Ala Pro Ser
            340                 345                 350

Ala Ser Leu Pro Ser Thr Pro Phe Asn Pro Phe Asn Asn Met Val Gly
            355                 360                 365

Trp Tyr Arg Gln Ala Pro Gly Lys Gln Arg Glu Met Val Ala Ser Ile
            370                 375                 380

Gly Leu Arg Ile Asn Tyr Ala Asp Ser Val Lys Gly Arg Phe Thr Ile
385                 390                 395                 400

Ser Arg Asp Asn Ala Lys Asn Thr Val Asp Leu Gln Met Asp Ser Leu
                405                 410                 415

Arg Pro Glu Asp Ser Ala Thr Tyr Tyr Cys His Ile Glu Tyr Thr His
            420                 425                 430

Tyr Trp Gly Lys Gly Thr Leu Val Thr Val Ser Ser Glu Pro Lys Thr
            435                 440                 445

Pro Lys Pro Gln Pro Ala Arg Gln Gly Ala Pro Val Pro Tyr Pro Asp
    450                 455                 460

Pro Leu Glu Pro Arg
465

<210> SEQ ID NO 53
<211> LENGTH: 109
<212> TYPE: PRT
<213> ORGANISM: Clostridium botulinum

<400> SEQUENCE: 53

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 54
<211> LENGTH: 15
<212> TYPE: PRT
<213> ORGANISM: Artificial Sequence
<220> FEATURE:
<223> OTHER INFORMATION: The sequence has been designed and synthesized

<400> SEQUENCE: 15

Gly Gly Gly Gly Ser Gly Gly Gly Ser Gly Gly Gly Gly Ser
1               5                   10                  15